(12) United States Patent
Malinin et al.

(10) Patent No.: US 11,148,997 B2
(45) Date of Patent: *Oct. 19, 2021

(54) METHODS OF MANUFACTURING TREPROSTINIL AND TREPROSTINIL DERIVATIVE PRODRUGS

(71) Applicant: Insmed Incorporated, Bridgewater, NJ (US)

(72) Inventors: Vladimir Malinin, Bridgewater, NJ (US); Walter Perkins, Bridgewater, NJ (US); Franziska Leifer, Bridgewater, NJ (US); Donna M. Konicek, Bridgewater, NJ (US); Zhili Li, Bridgewater, NJ (US); Adam Plaunt, Bridgewater, NJ (US)

(73) Assignee: INSMED INCORPORATED, Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/417,958

(22) Filed: May 21, 2019

(65) Prior Publication Data

US 2019/0337888 A1  Nov. 7, 2019

Related U.S. Application Data

(63) Continuation of application No. 15/527,811, filed as application No. PCT/US2015/061427 on Nov. 18, 2015, now Pat. No. 10,343,979.

(60) Provisional application No. 62/081,515, filed on Nov. 18, 2014.

(51) Int. Cl.
C07C 231/02 (2006.01)
C07C 67/08 (2006.01)

(52) U.S. Cl.
CPC ............ *C07C 231/02* (2013.01); *C07C 67/08* (2013.01); *C07C 2601/18* (2017.05); *C07C 2602/24* (2017.05)

(58) Field of Classification Search
None
See application file for complete search history.

(56) References Cited

U.S. PATENT DOCUMENTS

| 4,367,237 | A | 1/1983 | Wakatsuka et al. |
| 4,668,814 | A | 5/1987 | Aristoff |
| 4,837,342 | A | 6/1989 | Shibasaki et al. |
| 5,153,222 | A | 10/1992 | Tadepalli et al. |
| 5,190,972 | A | 3/1993 | Dumble |
| 5,234,953 | A | 8/1993 | Crow et al. |
| 5,662,932 | A | 9/1997 | Amselem et al. |
| 6,054,486 | A | 4/2000 | Crow et al. |
| 6,165,500 | A | 12/2000 | Ceva |
| 6,242,482 | B1 | 6/2001 | Shorr et al. |
| 6,306,435 | B1 | 10/2001 | Chen et al. |
| 6,521,212 | B1 | 2/2003 | Cloutier et al. |
| 6,756,033 | B2 | 6/2004 | Cloutier et al. |
| 6,803,386 | B2 | 10/2004 | Shorr et al. |
| 7,199,157 | B2 | 4/2007 | Wade et al. |
| 7,384,978 | B2 | 6/2008 | Phares et al. |
| 7,417,070 | B2 | 8/2008 | Phares et al. |
| 7,544,713 | B2 | 6/2009 | Phares et al. |
| 7,858,650 | B2 | 12/2010 | Yamamoto et al. |
| 7,879,909 | B2 | 2/2011 | Wade et al. |
| 7,999,007 | B2 | 8/2011 | Jeffs et al. |
| 8,242,305 | B2 | 8/2012 | Batra et al. |
| 8,349,892 | B2 | 1/2013 | Phares |
| 8,350,079 | B2 | 1/2013 | Walsh |
| 8,461,393 | B2 | 6/2013 | Sharma |
| 8,481,782 | B2 | 7/2013 | Batra et al. |
| 8,609,728 | B2 | 12/2013 | Rothblatt et al. |
| 8,969,409 | B2 | 3/2015 | Rothblatt et al. |
| 9,102,660 | B2 | 8/2015 | Batra et al. |
| 9,255,064 | B2 | 2/2016 | Malinin et al. |
| 9,469,600 | B2 | 10/2016 | Malinin et al. |
| 9,593,061 | B2 | 3/2017 | Batra et al. |
| 9,624,156 | B2 | 4/2017 | Phares et al. |
| 10,010,518 | B2 | 7/2018 | Malinin et al. |

(Continued)

FOREIGN PATENT DOCUMENTS

CN  101669904  3/2010
EP  0496548 A1  7/1992

(Continued)

OTHER PUBLICATIONS

Supplementary European Search Report for European Application No. 13859435.3, dated Mar. 29, 2016, 7 pages.
International Search Report and Written Opinion for International Application No. PCT/US2013/072647, dated Apr. 4, 2014, 9 pages.
International Search Report and Written Opinion for International Application No. PCT/US2015/019661, dated Jun. 3, 2015, 10 pages.
Extended European Search Report for European Application No. 14855785.3, dated May 22, 2017, 9 pages.
International Search Report and Written Opinion for International Application No. PCT/US2014/062232, dated Apr. 23, 2015, 11 pages.
Extended European Search Report for European Application No. 15862092.2, dated May 25, 2018, 8 pages.

(Continued)

*Primary Examiner* — Ana Z Muresan
(74) *Attorney, Agent, or Firm* — Cooley LLP

(57) ABSTRACT

Methods for making prodrugs of treprostinil and treprostinil derivatives are provided. Specifically, methods are provided herein for producing prostacyclin compounds comprising treprostinil covalently linked to a linear $C_5$-$C_{18}$ alkyl, branched $C_5$-$C_{18}$ alkyl, linear $C_2$-$C_{18}$ alkenyl, branched $C_3$-$C_{18}$ alkenyl, aryl, aryl-$C_1$-$C_{18}$ alkyl or an amino acid or a peptide (e.g., dipeptide, tripeptide, tetrapeptide). The linkage, in one embodiment, is via an amide or ester bond. Prostacyclin compounds provided herein can also include at least one hydrogen atom substituted with at least one deuterium atom. The compounds provided herein can be used to treat pulmonary hypertension (e.g., pulmonary arterial hypertension) and portopulmonary hypertension.

17 Claims, 1 Drawing Sheet

(56) References Cited

U.S. PATENT DOCUMENTS

| | | |
|---|---|---|
| 10,343,979 B2 | 7/2019 | Malinin et al. |
| 10,526,274 B2 | 1/2020 | Malinin et al. |
| 2003/0022242 A1 | 1/2003 | Anderson |
| 2003/0108512 A1 | 6/2003 | Shorr et al. |
| 2003/0108743 A1 | 6/2003 | Anderson |
| 2004/0156816 A1 | 8/2004 | Anderson |
| 2005/0085540 A1 | 4/2005 | Phares et al. |
| 2005/0165111 A1 | 7/2005 | Wade et al. |
| 2005/0282901 A1 | 12/2005 | Phares et al. |
| 2005/0282903 A1 | 12/2005 | Wade et al. |
| 2007/0078095 A1 | 4/2007 | Phares et al. |
| 2008/0200449 A1 | 8/2008 | Olschewski et al. |
| 2008/0202513 A1 | 8/2008 | Birchall et al. |
| 2008/0249167 A1 | 10/2008 | Phares et al. |
| 2008/0280986 A1 | 11/2008 | Wade et al. |
| 2009/0036465 A1 | 2/2009 | Roscigno et al. |
| 2009/0074828 A1 | 3/2009 | Alexis et al. |
| 2010/0076083 A1 | 3/2010 | Olschewski et al. |
| 2010/0324313 A1 | 12/2010 | Hogan et al. |
| 2012/0004307 A1 | 1/2012 | Wade et al. |
| 2012/0010159 A1 | 1/2012 | Rothblatt et al. |
| 2012/0216801 A1 | 8/2012 | Olschewski et al. |
| 2013/0053581 A1 | 2/2013 | Wei et al. |
| 2013/0184295 A1 | 7/2013 | Sprague et al. |
| 2013/0261187 A1 | 10/2013 | Phares et al. |
| 2014/0193379 A1 | 7/2014 | Jeffs et al. |
| 2014/0256730 A1 | 9/2014 | Becker et al. |
| 2014/0275262 A1 | 9/2014 | Phares et al. |
| 2014/0275616 A1 | 9/2014 | Batra et al. |
| 2014/0323567 A1 | 10/2014 | Laing |
| 2015/0005374 A1 | 1/2015 | Phares et al. |
| 2015/0148414 A1 | 5/2015 | Malinin et al. |
| 2015/0166503 A1 | 6/2015 | Becker et al. |
| 2015/0175529 A1 | 6/2015 | Malinin et al. |
| 2015/0328232 A1 | 11/2015 | Malinin et al. |
| 2016/0235742 A1 | 8/2016 | Zisman |
| 2016/0256425 A1 | 9/2016 | Malinin et al. |
| 2016/0318844 A1 | 11/2016 | Malinin et al. |
| 2017/0049739 A1 | 2/2017 | Plaunt et al. |
| 2017/0320813 A1 | 11/2017 | Malinin et al. |
| 2018/0153847 A1 | 6/2018 | Phares et al. |
| 2019/0248731 A1 | 8/2019 | Malinin et al. |
| 2020/0079724 A1 | 3/2020 | Malinin et al. |
| 2020/0338005 A1 | 10/2020 | Du et al. |

FOREIGN PATENT DOCUMENTS

| | | |
|---|---|---|
| EP | 0989108 A2 | 3/2000 |
| EP | 1161234 B1 | 7/2003 |
| EP | 1045695 B1 | 3/2004 |
| EP | 1696932 B1 | 9/2009 |
| EP | 1744739 B1 | 3/2010 |
| EP | 1696900 B1 | 7/2010 |
| EP | 2461812 B1 | 1/2014 |
| EP | 2792353 A2 | 10/2014 |
| EP | 2200650 B1 | 1/2016 |
| JP | S61-289034 | 12/1986 |
| JP | H08-507515 | 8/1996 |
| JP | 2002-521423 | 7/2002 |
| JP | 2002-539154 | 11/2002 |
| JP | 2006-528969 | 12/2006 |
| JP | 2007-501281 | 1/2007 |
| JP | 2008-507585 | 3/2008 |
| JP | 2009-519972 | 5/2009 |
| JP | 2009-537246 | 10/2009 |
| JP | 2012-516187 | 7/2012 |
| WO | WO 99/033490 | 7/1999 |
| WO | WO 2000/006120 | 2/2000 |
| WO | WO 2000/057701 | 10/2000 |
| WO | WO 2004/103348 | 12/2004 |
| WO | WO 2005/007081 | 1/2005 |
| WO | WO 2008/098196 | 8/2008 |
| WO | WO 2009/152160 | 12/2009 |
| WO | WO 2009/158010 | 12/2009 |
| WO | WO 2010/036798 | 4/2010 |
| WO | WO 2010/039531 | 4/2010 |
| WO | WO 2010/129757 | 11/2010 |
| WO | WO 2011/003058 | 1/2011 |
| WO | WO 2011/022707 | 2/2011 |
| WO | WO 2011/089215 | 7/2011 |
| WO | WO 2011/089216 | 7/2011 |
| WO | WO 2011/153363 | 12/2011 |
| WO | WO 2012/009816 | 1/2012 |
| WO | WO 2012/107364 | 8/2012 |
| WO | WO 2012/111627 | 8/2012 |
| WO | WO 2012/124688 | 9/2012 |
| WO | WO 2013/024047 | 2/2013 |
| WO | WO 2013/024048 | 2/2013 |
| WO | WO 2013/024049 | 2/2013 |
| WO | WO 2013/024051 | 2/2013 |
| WO | WO 2013/024052 | 2/2013 |
| WO | WO 2013/024053 | 2/2013 |
| WO | WO 2013/174848 | 11/2013 |
| WO | WO 2014/022373 | 2/2014 |
| WO | WO 2014/022376 | 2/2014 |
| WO | WO 2014/045813 | 6/2014 |
| WO | WO 2014/110094 | 7/2014 |
| WO | WO 2014/110491 | 7/2014 |
| WO | WO 2014/203278 | 12/2014 |
| WO | WO 2015/061720 | 4/2015 |
| WO | WO 2015/138423 | 9/2015 |
| WO | WO 2015/192030 | 12/2015 |
| WO | WO 2016/081658 | 5/2016 |
| WO | WO 2017/192993 | 11/2017 |
| WO | WO 2017/223400 | 12/2017 |
| WO | WO-2020136276 A1 | 7/2020 |

OTHER PUBLICATIONS

International Search Report and Written Opinion for International Application No. PCT/US2015/061427, dated Feb. 2, 2016, 9 pages.

International Search Report and Written Opinion for International Application No. PCT/US2017/038932, dated Sep. 21, 2017, 10 pages.

Channick, R. N. et al., "Inhaled treprostinil: a therapeutic review," Drug Design, Development and Therapy, 2012:6, p. 19-28.

Kleemann, E. et al., "Iloprost-containing liposomes for aerosol application in pulmonary arterial hypertension: formulation aspects and stability," Pharmaceutical Research, 24(2):277-287, Feb. 2007, Epub Dec. 2006.

Kuo, Y-C. et al., "Physicochemical properties of nevirapine-loaded solid lipid nanoparticles and nanostructured lipid carriers," Colloids and Surfaces B: Biointerfaces 83 (2011) 299-306.

Leifer, F. et al., "Prolonged activity of inhaled treprostinil prodrug nanoparticles in a rat model of pulmonary arterial hypertension," Poster presented at the European Respiratory Society (ERS) International Congress, Sep. 6-10, 2014, Munich, Germany. Retrieved from the Internet: <URL: http://www.insmed.com/pdf/3-ProlongedInhaledTreprostinil.pdf>. [Retrieved on May 4, 2017], 1 page.

Lehofer, B., Master's Thesis, "Investigation of liposomal formulations suitable for pulmonary application of iloprost with different nebulizer devices," Graz University of Technology, Feb. 2013, [Online], Retrieved from the Internet: <URL: http://diglib.tugraz.at/download.php?id=576a742a427d7&location=browse>, 117 pages.

Mayo Clinic [online], "Pulmonary Fibrosis, Symptoms and Causes," Retrieved from the Internet on Dec. 15, 2016, <URL: http://www.mayoclinic.org/diseases-conditions/pulmonary-fibrosis/symptoms-causes/dxc-20211754>, 5 pages.

McLaughlin, V. V. et al., "Addition of inhaled treprostinil to oral therapy for pulmonary arterial hypertension," Journal of the American College of Cardiology, 55(18):1915-1922 (2010).

Moriarty, R. M. et al., "The intramolecular asymmetric pauson-khand cyclization as a novel and general stereoselective route to benzindene prostacyclins: synthesis of UT-15 (treprostinil)," J. Org. Chem., 69(6):1890-1902 (2004).

Muller, R. H. et al., "Solid lipid nanoparticles (SLN) for controlled drug delivery—a review of the state of the art," European Journal of Pharmaceutics and Biopharmaceutics, 50 (2000) 161-177.

Poms, A. et al., "Inhaled Treprostinil for the treatment of Pulmonary Arterial Hypertension," Critical Care Nurse, 31(6):e1-e11 (2009).

(56) References Cited

OTHER PUBLICATIONS

Provencher, S., "Long-term treprostinil in pulmonary arterial hypertension: is the glass half full or half empty'?," Eur. Respir. J., 28(6):1073-1075 (2006).
Saleemi, S., "Portopulmonary hypertension," Ann. Thorac Med., 5(1):5-9 (Jan.-Mar. 2010).
Skoro-Sajer, N. et al., "Treprostinil for pulmonary hypertension," Vascular Health and Risk Management, 4(3):507-513 (2008).
Sorbera, L. A. et al., "UT-15. Treatment of pulmonary hypertension treatment of peripheral vascular disease," Drug of the Future, 26(4):364-374 (2001).
PubChem Substance of Record for UNII-8GJK87S89F, PubChem CID: 91617675, published online Mar. 18, 2015, pp. 1-8.
Mosgoeller, W. et al., "Nanoparticle-Mediated Treatment of Pulmonary Arterial Hypertension," Chapter 17 In: Methods in Enzymology, vol. 508, (2012) pp. 325-354.
Oberdorster, G. et al., "Nanotoxicology: An emerging discipline evolving from studies of ultrafine particles," Environmental Health Perspectives, vol. 113, No. 7, pp. 823-839 (Jul. 2005).
Vieira, D. B. et al., "Assembly of a model hydrophobic drug into cationic bilayer fragments," Journal of Colloid and Interface Science, vol. 293, pp. 240-247 (2006).
Sriwongsitanont, S. et al., "Effect of PEG Lipid (DSPE-PEG2000) and freeze-thawing process on the phospholipid vesicle size and lamellarity," Colloid Polymer Science, vol. 282, No. 7, pp. 753-760 (May 2004); published online Dec. 3, 2003.
International Search Report and Written Opinion for International Application No. PCT/US2020/030282, dated Aug. 4, 2020, 8 pages.
Shorr, A. F. et al., "Pulmonary hypertension in patients with pulmonary fibrosis awaiting lung transplant," Eur. Respir. J., 2007, vol. 30, pp. 715-721 (2007).
Kunishima, M., "The studies on reaction control and development of new practical reagents based on characteristics of reaction field," The Pharmaceutical Society of Japan, 128(3):425-438 (2008) (with English Abstract).
Hassan, A. et al., "Medium effect on the second-stage dissociation constant of N-(2-acetamido)imino diacetic acid (H2ADA)," Canadian Journal of Chemistry 70(6):1684-1687 (1992).
Bard, A. J., "The electrochemistry of organic compounds in aprotic solvents—methods and applications," Pure and Applied Chemistry, vol. 25, Issue 2, pp. 379-393 (Jan. 1971).
Atkins, P. J., "Dry Powder Inhalers: An Overview," Conference Proceedings, Respiratory Care, 50(10):1304-1312 (Oct. 2005).
Extended European Search Report for European Application No. 20213903.6, dated Mar. 22, 2021, 7 pages.
Adi, H et al., "Co-spray-dried mannitol-ciprofloxacin dry powder inhaler formulation for cystic fibrosis and chronic obstructive pulmonary disease," European Journal of Pharmaceutical Sciences, vol. 40, pp. 239-247 (2010).
Extended European Search Report for European Application No. 21164646.8, dated Jul. 21, 2021, 8 pages.
International Search Report and Written Opinion for International Application No. PCT/US2021/024077, dated Jul. 28, 2021, 11 pages.
Leifer, F. G et al., "Inhaled Treprostinil-Prodrug Lipid Nanoparticle Formulations Provide Long-Acting Pulmonary Vasodilation," Drug Res (Stuttg) 2018; 68(11):605-614.
Mangal, S. et al., "Physico-Chemical Properties, Aerosolization and Dissolution of Co-Spray Dried Azithromycin Particles with L-Leucine for Inhalation," Pharmaceutical Research (2018) 35:28; 15 pages.
Shetty, N. et al., "Influence of excipients on physical and aerosolization stability of spray dried high-dose powder formulations for inhalation," Int. J. Pharm, Jun. 2018, 544(1):222-234.
Strickley, R. G., "Solubilizing excipients in oral and injectable formulations," Pharmaceutical Research, Feb. 2004, vol. 21, No. 2, pp. 201-230.

METHODS OF MANUFACTURING TREPROSTINIL AND TREPROSTINIL DERIVATIVE PRODRUGS

CROSS REFERENCE TO RELATED APPLICATION

This application is a continuation of U.S. application Ser. No. 15/527,811, filed May 18, 2017, now U.S. Pat. No. 10,343,979, which is a national phase of International Application No. PCT/US2015/061427, filed Nov. 18, 2015, which claims priority from U.S. Provisional Application Ser. No. 62/081,515, filed Nov. 18, 2014, the disclosure of each of which is incorporated by reference herein in its entirety for all purposes.

BACKGROUND OF THE INVENTION

Pulmonary hypertension (PH) is characterized by an abnormally high blood pressure in the lung vasculature. It is a progressive, lethal disease that leads to heart failure and can occur in the pulmonary artery, pulmonary vein, or pulmonary capillaries. Symptomatically patients experience shortness of breath, dizziness, fainting, and other symptoms, all of which are made worse by exertion. There are multiple causes, and can be of unknown origin, idiopathic, and can lead to hypertension in other systems, for example, portopulmonary hypertension in which patients have both portal and pulmonary hypertension.

Pulmonary hypertension has been classified into five groups by the World Health Organization (WHO). Group I is called pulmonary arterial hypertension (PAH), and includes PAH that has no known cause (idiopathic), inherited PAH (i.e., familial PAH or FPAH), PAH that is caused by drugs or toxins, and PAH caused by conditions such as connective tissue diseases, HIV infection, liver disease, and congenital heart disease. Group II pulmonary hypertension is characterized as pulmonary hypertension associated with left heart disease. Group III pulmonary hypertension is characterized as PH associated with lung diseases, such as chronic obstructive pulmonary disease and interstitial lung diseases, as well as PH associated with sleep-related breathing disorders (e.g., sleep apnea). Group IV PH is PH due to chronic thrombotic and/or embolic disease, e.g., PH caused by blood clots in the lungs or blood clotting disorders. Group V includes PH caused by other disorders or conditions, e.g., blood disorders (e.g., polycythemia vera, essential thrombocythemia), systemic disorders (e.g., sarcoidosis, vasculitis), metabolic disorders (e.g., thyroid disease, glycogen storage disease).

Pulmonary arterial hypertension (PAH) afflicts approximately 200,000 people globally with approximately 30,000-40,000 of those patients in the United States. PAH patients experience constriction of pulmonary arteries which leads to high pulmonary arterial pressures, making it difficult for the heart to pump blood to the lungs. Patients suffer from shortness of breath and fatigue which often severely limits the ability to perform physical activity.

The New York Heart Association (NYHA) has categorized PAH patients into four functional classes, used to rate the severity of the disease. Class I PAH patients as categorized by the NYHA, do not have a limitation of physical activity, as ordinary physical activity does not cause undue dyspnoea or fatigue, chest pain, or near syncope. Treatment is not needed for class I PAH patients. Class II PAH patients as categorized by the NYHA have a slight limitation on physical activity. These patients are comfortable at rest, but ordinary physical activity causes undue dyspnoea or fatigue, chest pain or near syncope. Class III PAH patients as categorized by the NYHA have a marked limitation of physical activity. Although comfortable at rest, class III PAH patients experience undue dyspnoea or fatigue, chest pain or near syncope as a result of less than ordinary physical activity. Class IV PAH patients as categorized by the NYHA are unable to carry out any physical activity without symptoms. Class IV PAH patients might experience dyspnoea and/or fatigue at rest, and discomfort is increased by any physical activity. Signs of right heart failure are often manifested by class IV PAH patients.

Patients with PAH are treated with an endothelin receptor antagonist (ERA), phosphodiesterase type 5 (PDE-5) inhibitor, a guanylate cyclase stimulator, a prostanoid (e.g., prostacyclin), or a combination thereof. ERAs include abrisentan (Letairis®), sitaxentan, bosentan (Tracleer®), and macitentan (Opsumit®). PDE-5 inhibitors indicated for the treatment of PAH include sildenafil (Revatio®), tadalafil (Adcirca®). Prostanoids indicated for the treatment of PAH include iloprost, epoprosentol and treprostinil (Remodulin®, Tyvaso®). The one approved guanylate cyclase stimulator is riociguat (Adempas®). Additionally, patients are often treated with combinations of the aforementioned compounds.

Portopulmonary hypertension is defined by the coexistence of portal and pulmonary hypertension, and is a serious complication of liver disease. The diagnosis of portopulmonary hypertension is based on hemodynamic criteria: (1) portal hypertension and/or liver disease (clinical diagnosis-ascites/varices/splenomegaly), (2) mean pulmonary artery pressure >25 mmHg at rest, (3) pulmonary vascular resistance >240 dynes s/cm$^5$, (4) pulmonary artery occlusion pressure <15 mmHg or transpulmonary gradient >12 mmHg. PPH is a serious complication of liver disease, and is present in 0.25 to 4% of patients suffering from cirrhosis. Today, PPH is comorbid in 4-6% of those referred for a liver transplant.

Despite there being treatments for PAH and PPH, the current prostacyclin therapies are associated with severe toxicity and tolerability issues, as well as the requirement for inconvenient dosing schedules. The present invention overcomes addresses these factors by providing compounds and that provide for less toxicity, better tolerability and more convenient dosing schedules, and methods for manufacturing the same.

SUMMARY OF THE INVENTION

Methods for the manufacture of treprostinil prodrugs and treprostinil derivative prodrugs are provided herein, e.g., compounds of the Formulae (I), (II) or (III). The treprostinil or treprostinil derivative prodrug, in one embodiment, comprises an ester or amide linkage to the prodrug moiety.

One aspect of the invention relates to the synthesis of a carboxylic acid derivative of treprostinil. In one embodiment, a treprostinil ester derivative of the formula

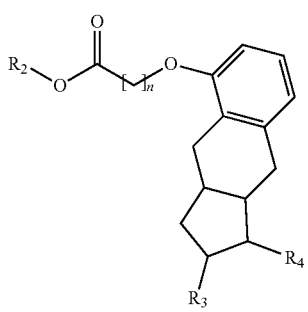

is esterified by mixing the appropriate alcohol (i.e., $R_2$—OH where the $R_2$ is a linear or branched $C_5$-$C_{18}$ alkyl, a linear $C_2$-$C_{18}$ alkenyl or a branched $C_3$-$C_{18}$ alkenyl) with treprostinil or a compound of the formula

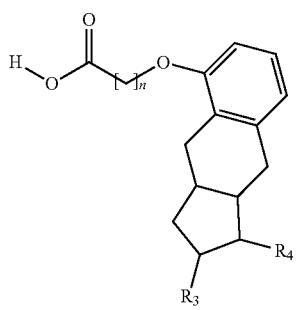

in the presence of an acid catalyst. The acid catalyst in one embodiment is a resin or in some other solid form. The acid catalyst in one embodiment is sulfuric acid or sulfonic acid. Other acid catalysts (in solid, e.g., a resin, or liquid form) include but are not limited to hydrofluoric acid, phosphoric acid, toluenesulfonic acid, polystyrene solfonate, hyeteropoly acid, zeolites, metal oxides, and graphene oxygene In some embodiments, the treprostinil or treprostinil compound of the formula

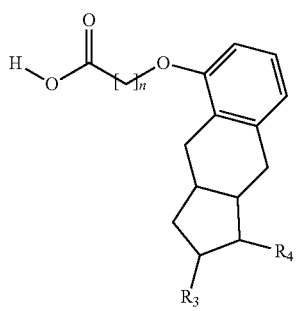

(where $R_3$, $R_4$ and n are defined above) and/or alcohol $R_2$—OH is dissolved in a solvent prior to the esterification reaction.

In another embodiment, the Mitsunobu reaction can be used, where a mixture of triphenylphosphine (PPh$_3$) and diisoporpyl azodicarboxylate (DIAD or its diethyl analogue, DEAD) convert an alcohol and carboxylic acid to the ester to form one of the carboxylic acid ester prodrugs provided herein.

In yet another embodiment, N, N'-dicyclohexylcarbodiimide (DCC) or N, N'-diisopropylcarbodiimide (DIC) is used in combination with 4-dimethylaminopyridine (DMAP) in an esterification reaction (sometimes referred to as Steglich esterification).

Treprostinil amide derivatives (e.g., of the formula:

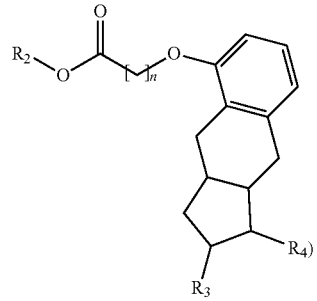

can be manufactured according to well known protocols of amide functionalization of a carboxylic acid group. For example, treprostinil (or a compound of the formula

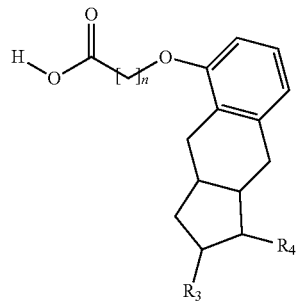

(for example, dissolved in dioxane) is combined with HATU or PyBOP and alkylamine $R_2$—NH$_2R_2$, $R_3$, $R_4$ and n are defined herein.

The methods provided herein in one embodiment, are used to manufacture a prostacyclin compound of Formula (I), or a pharmaceutically acceptable salt:

Formula (I)

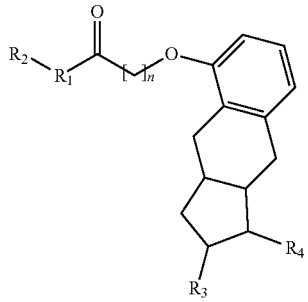

wherein $R_1$ is NH, O or S; $R_2$ is H, a linear $C_5$-$C_{18}$ alkyl, branched $C_5$-$C_{18}$ alkyl, linear $C_2$-$C_{18}$ alkenyl, branched $C_3$-$C_{18}$ alkenyl, aryl; aryl-$C_1$-$C_{18}$ alkyl; an amino acid or a peptide; $R_3$ is H, OH, O-alkyl or O-alkenyl; $R_4$ is an optionally substituted linear or branched $C_1$-$C_{15}$ alkyl, or an optionally substituted linear or branched $C_2$-$C_{15}$ alkenyl; and n is an integer from 0 to 5, with the proviso that the prostacyclin compound is not treprostinil.

In another embodiment, a method provided herein is used to manufacture a prostacyclin compound of Formula (II), or a pharmaceutically acceptable salt:

Formula (II)

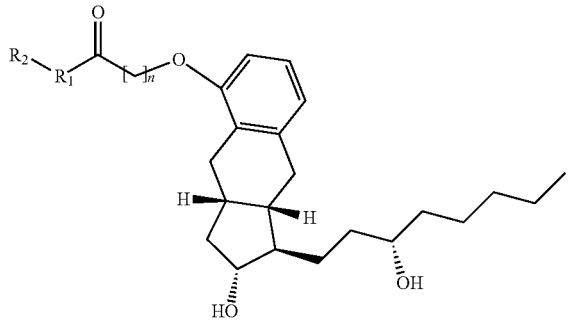

wherein $R_1$ is NH, O or S; $R_2$ is a linear or branched $C_5$-$C_{18}$ alkyl, a linear $C_2$-$C_{18}$ alkenyl or a branched $C_3$-$C_{18}$ alkenyl, aryl, aryl-$C_1$-$C_{18}$ alkyl, an amino acid or a peptide; and n is an integer from 0 to 5.

In one embodiment, a compound of Formula (I) and/or (II) is manufactured by a method described herein, wherein one or more hydrogen atoms is substituted with a deuterium. Accordingly, in one embodiment, the present invention relates to an isotopologue of Formula (I) and/or (II), substituted with one or more deuterium atoms. The isotopologue of Formula (I) and/or (II) may be used to accurately determine the concentration of compounds of Formula (I) and/or (II) in biological fluids and to determine metabolic patterns of compounds of Formula (I) and/or (II) and its isotopologues.

Yet another embodiment of the invention relates to a method for manufacturing the prostacyclin compound of Formula (III), or a pharmaceutically acceptable salt:

Formula (III)

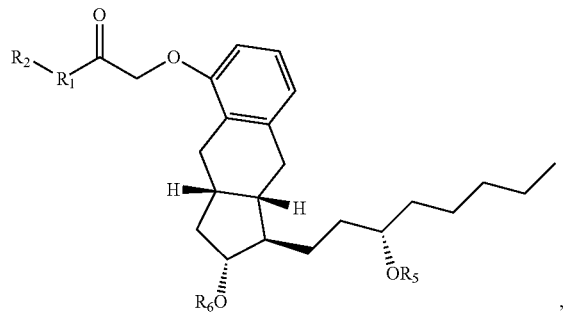

wherein $R_1$ and $R_2$ are defined above, and $R_5$ and $R_6$ are independently selected from H, optionally substituted linear or branched $C_1$-$C_{15}$ alkyl, optionally substituted linear or branched $C_2$-$C_{15}$ alkenyl, (C=O)-optionally substituted linear or branched $C_1$-$C_{15}$ alkyl, or (C=O)-optionally substituted linear or branched $C_2$-$C_{15}$ alkenyl, with the proviso that the prostacyclin compound of Formula (III) is not treprostinil.

DETAILED DESCRIPTION OF THE INVENTION

Figure 1:
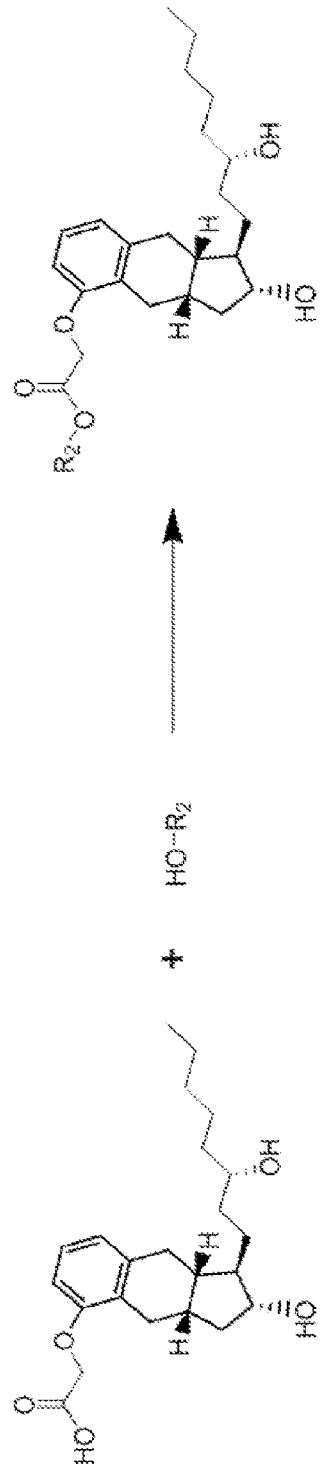
FIG. 1 is an esterification scheme for an alkyl ester-TR prodrug compound provided herein.

The term "alkyl" as used herein refers to both a straight chain alkyl, wherein alkyl chain length is indicated by a range of numbers, and a branched alkyl, wherein a branching point in the chain exists, and the total number of carbons in the chain is indicated by a range of numbers. In exemplary embodiments, "alkyl" refers to an alkyl chain as defined above containing 6, 7, 8, 9, 10, 11, 12, 13, 14, 15, 16 carbons (i.e., $C_6$-$C_{16}$ alkyl).

The term "alkenyl" as used herein refers to a carbon chain containing one or more carbon-carbon double bonds.

The term "aryl" as used herein refers to a cyclic hydrocarbon, where the ring is characterized by delocalized π electrons (aromaticity) shared among the ring members, and wherein the number of ring atoms is indicated by a range of numbers. In exemplary embodiments, "aryl" refers to a cyclic hydrocarbon as described above containing 6, 7, 8, 9, or 10 ring atoms (i.e., $C_6$-$C_{10}$ aryl). Examples of an aryl group include, but are not limited to, benzene, naphthalene, tetralin, indene, and indane.

The term "alkoxy" as used herein refers to —O-(alkyl), wherein "alkyl" is as defined above.

The term "substituted" in connection with a moiety as used herein refers to a further substituent which is attached to the moiety at any acceptable location on the moiety. Unless otherwise indicated, moieties can bond through a carbon, nitrogen, oxygen, sulfur, or any other acceptable atom.

The term "amino acid" refers to both natural (genetically encoded) and non-natural (non-genetically encoded) amino acids, and moieties thereof. Of the twenty natural amino acids, 19 have the general structure:

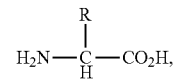

where R is the amino acid sidechain. The 20$^{th}$ amino acid, proline, is also within the scope of the present invention, and has the following structure:

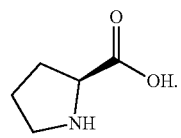

Of the twenty natural amino acids, all but glycine is chiral, and both the D- and L-amino acid isomers, as well as mixtures thereof, are amenable for use with the prostacyclin compounds described herein. It is also noted that an amino acid moiety is encompassed by the term "amino acid." For example, the amino acid moieties

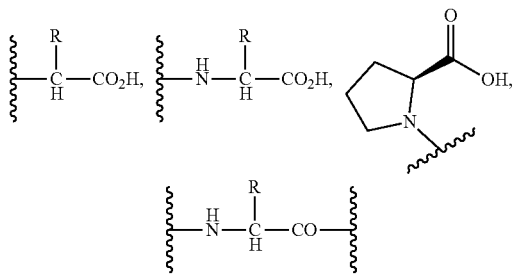

are encompassed by the term "amino acid."

Examples of non-natural amino acids amenable for use with the present invention include β-alanine (13-Ala); 2,3-diaminopropionic acid (Dpr); nipecotic acid (Nip); pipecolic acid (Pip); ornithine (Orn); citrulline (Cit); t-butylalanine (t-BuA); 2-tbutylglycine (t-BuG); N-methylisoleucine (MeIle); phenylglycine (PhG); cyclohexylalanine (ChA); norleucine (Nle); naphthylalanine (Nal); 4-chlorophenylalanine (Phe(4-Cl)); 2-fluorophenylalanine (Phe(2-F)); 3-fluorophen ylalanine (Phe(3-F)); 4-fluorophenylalanine (Phe(4-F)); penicillamine (Pen); 1,2,3,4-tetrahydroisoquinoline-3-carboxylic acid (Tic); β-2-thienylalanine (Thi); methionine sulfoxide (MSO); homoarginine (hArg); N-acetyllysine (AcLys); 2,4-diaminobutyric acid (Dbu); 2,3-diaminobutyric acid (Dab); p-aminophenylalanine (Phe (pNH2)); N-methyl valine (MeVal); homocysteine (hCys), homophenylalanine (hPhe); homoserine (hSer); hydroxyproline (Hyp); homoproline (hPro); and the corresponding D-enantiomer of each of the foregoing. Other non-genetically encoded amino acid residues include 3-aminopropionic acid; 4-aminobutyric acid; isonipecotic acid (Inp); aza-pipecolic acid (azPip); aza-proline (azPro); α-aminoisobutyric acid (Aib); ε-aminohexanoic acid (Aha); δ-aminovaleric acid (Ava); N-methylglycine (MeGly).

A "peptide" is a polymer of amino acids (or moieties thereof) linked by a peptide bond. Peptides for use with the present invention, comprise from about two to about fifteen amino acids, for example, two, three, four, five, six, seven, eight, nine or ten amino acids (or moieties thereof).

The term "salt" or "salts" as used herein encompasses pharmaceutically acceptable salts commonly used to form alkali metal salts of free acids and to form addition salts of free bases. The nature of the salt is not critical, provided that it is pharmaceutically acceptable. Suitable pharmaceutically acceptable acid addition salts may be prepared from an inorganic acid or from an organic acid. Exemplary pharmaceutical salts are disclosed in Stahl, P. H., Wermuth, C. G., Eds. *Handbook of Pharmaceutical Salts: Properties, Selection and Use*; Verlag Helvetica Chimica Acta/Wiley-VCH: Zurich, 2002, the contents of which are hereby incorporated by reference in their entirety. Specific non-limiting examples of inorganic acids are hydrochloric, hydrobromic, hydroiodic, nitric, carbonic, sulfuric and phosphoric acid. Appropriate organic acids include, without limitation, aliphatic, cycloaliphatic, aromatic, arylaliphatic, and heterocyclyl containing carboxylic acids and sulfonic acids, for example formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, 3-hydroxybutyric, galactaric or galacturonic acid. Suitable pharmaceutically acceptable salts of free acid-containing compounds disclosed herein include, without limitation, metallic salts and organic salts. Exemplary metallic salts include, but are not limited to, appropriate alkali metal (group Ia) salts, alkaline earth metal (group IIa) salts, and other physiological acceptable metals. Such salts can be made from aluminum, calcium, lithium, magnesium, potassium, sodium and zinc. Exemplary organic salts can be made from primary amines, secondary amines, tertiary amines and quaternary ammonium salts, for example, tromethamine, diethylamine, tetra-N-methylammonium, N,N'-dibenzylethylenediamine, chloroprocaine, choline, diethanolamine, ethylenediamine, meglumine (N-methylglucamine) and procaine.

Methods are provided herein for the synthesis of treprostinil prodrugs, as well as treprostinil derivative prodrugs, for example prodrugs of Formulae (I), (II) and (III). The prodrugs find utility in the treatment of pulmonary hypertension, for example, pulmonary arterial hypertension and portopulmonary hypertension, as well as other indications, as described in U.S. Patent Application Publication No. 2015/0148414, published May 28, 2015, the disclosure of which is incorporated by reference in its entirety for all purposes., For example, the treprostinil derivative prodrug or treprostinil prodrug, or a composition comprising the same, is effective when employed in a once-daily, twice-daily or three-times daily dosing regimen, for example, for the treatment of pulmonary arterial hypertension or portopulmonary hypertension in a patient in need thereof. The prostacyclin compound provided herein, in one embodiment, can be administered less frequently than treprostinil, with equal or greater efficacy. Moreover, in one embodiment, the side effect profile of the compounds provided herein is less deleterious than the side effect profile resulting from treprostinil administration.

One aspect of the invention relates to the synthesis of a carboxylic acid derivative of treprostinil. In one embodiment, a treprostinil ester derivative of the formula

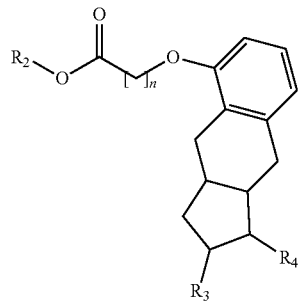

is esterified by mixing the appropriate alcohol (i.e., $R_2$—OH where the $R_2$ is a linear or branched $C_5$-$C_{18}$ alkyl, a linear $C_2$-$C_{18}$ alkenyl or a branched $C_3$-$C_{18}$ alkenyl) with treprostinil or a compound of the formula

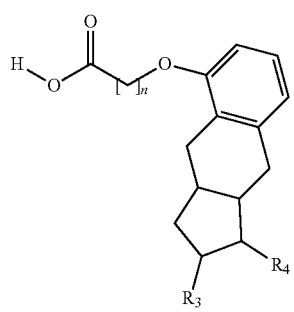

in the presence of an acid catalyst. As provided herein, $R_3$ is H, OH, optionally substituted linear or branched $C_1$-$C_{15}$ alkyoxy, O-optionally substituted linear or branched $C_2$-$C_{15}$ alkenyl, O—(C═O)-optionally substituted linear or branched $C_1$-$C_{15}$ alkyl, or O—(C═O)-optionally substituted linear or branched $C_2$-$C_{15}$ alkenyl; $R_4$ is an optionally substituted linear or branched $C_1$-$C_{15}$ alkyl, or an optionally substituted linear or branched $C_2$-$C_{15}$ alkenyl; and n is an integer from 0 to 5. It will be appreciated by one of ordinary skill in the art that the purity of the final product will depend in part on the purity of the reagents employed in the esterification reaction, and/or the cleanup procedure after the reaction has completed. For example, a high purity alcohol will give a higher purity treprostinil ester derivative than a lower purity alcohol. Similarly, a higher purity product is obtained through clean-up procedures such as HPLC, dia-filtration, etc.

The acid catalyst in one embodiment is a resin or in some other solid form. However, in other embodiment, the acid catalyst is in liquid form. The acid catalyst in one embodiment is sulfuric acid or sulfonic acid. Other acid catalysts (in solid, e.g., a resin, or liquid form) include but are not limited to hydrofluoric acid, phosphoric acid, toluenesulfonic acid, polystyrene solfonate, hyeteropoly acid, zeolites, metal oxides, and graphene oxygene.

Acid catalyst resins, e.g., sulfonic acid resin catalysts are available commercially, e.g., from Sigma-Aldrich, under the trade name AMBERLYST. Other resins are available commercially, e.g., from Purolite®, and are amenable for use with the methods described herein.

In some embodiments, the treprostinil or the treprostinil compound of the formula

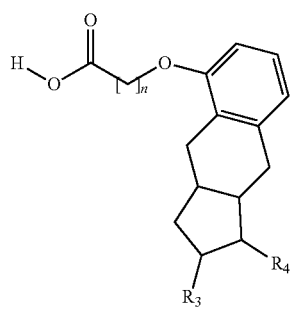

(where $R_3$, $R_4$ and n are defined above) and/or alcohol $R_2$—OH is dissolved in a solvent prior to the esterification reaction. For example, in one embodiment, where treprostinil is esterified with an alkyl group having 12 carbon atoms or more, treprostinil is first dissolved in a solvent such as dioxane prior to the esterification reaction. Other solvents besides dioxane, or in combination with dioxane can also be used. For example, acetonitrile (MeCN), N,N'-dimethylformamide (DMF), dichloromethane (DCM), or a combination thereof can be used. Various examples of solvents are provided in Table 1 below.

TABLE 1

| Solvents amenable for use in esterification reactions. |
|---|
| Dioxane |
| Dioxane (2 mL/100 µmol TRP) |
| Dioxane (1 mL/100 µmol TRP) |
| DMF |
| DCM |
| MeCN |
| 1:1 Dioxane:MeCN |
| DMF/DCM |
| 10% DMF/DCM |
| 20% DMF/DCM |

Carboxylic acid esterification reactions other than the ones described above are known to those of ordinary skill in the art and are amenable for use in manufacturing the treprostinil alkyl esters described herein. For example, the Mitsunobu reaction can be used, where a mixture of triphenylphosphine ($PPh_3$) and diisoporpyl azodicarboxylate (DIAD or its diethyl analogue, DEAD) convert an alcohol and carboxylic acid to the ester. In this reaction, the DIAD is reduced as it serves as the hydrogen acceptor, and the $PPh_3$ is oxidized to $OPPh_3$.

In yet another embodiment, N, N'-dicyclohexylcarbodiimide (DCC) or N, N'-diisopropylcarbodiimide (DIC) is used in combination with 4-dimethylaminopyridine (DMAP) (additive) in an esterification reaction (sometimes referred to as Steglich esterification). In this reaction, DCC or DIC and the carboxylic acid (treprostinil or its non-esterified derivative) are able to form an O-acylisourea activated carboxylic acid intermediate. The alcohol is added to the activated compound to form the stable dicyclohexylurea and the ester. In one embodiment, the treprostinil or its non-esterified derivative is first dissolved in solvent, e.g., one of the solvents described above, prior to performing the Steglich esterification.

Other esterification reactions can be employed. For example, 1-[Bis (dimethylamino) methylene]-1H-1,2,3-triazolo[4,5-b]pyridinium 3-oxid hexafluorophosphate (HATU) or benzotriazol-1-yl-oxytripyrrolidinophosphonium hexafluorophosphate (PyBOP) can be used as a coupling reagent. These reagents can be used with or without an additive to facilitate the coupling. For example, triethylamine (TEA) can be used in some embodiments in conjunction with either HATU or PyBOP coupling reagents to form a treprostinil alkyl ester. As with the other esterification reactions described herein, the treprostinil or non-esterified treprostinil derivative can first be dissolved in solvent prior to performing the esterification reaction.

In yet another embodiment, an esterification of treprostinil or a treprostinil derivative proceeds through steps 1 through 5 of the reaction scheme set forth in Example 3 of PCT Publication No. WO 2011/153363, incorporated by reference herein in its entirety for all purposes.

Treprostinil amide derivatives (e.g., of the formula:

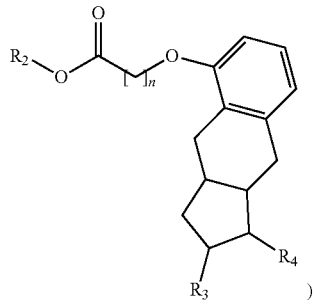

can be manufactured according to protocols of amide functionalization of a carboxylic acid group. For example, treprostinil (or a compound of the formula

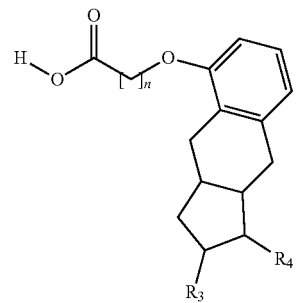

(for example, dissolved in dioxane) is combined with HATU or PyBOP and alkylamine $R_2$—$NH_2$ $R_2$, $R_3$, $R_4$ and n are defined above.

Other reaction conditions for forming treprostinil amide derivatives with alkylamine $R_2$—$NH_2$, are provided below in Table 2.

TABLE 2

| Entry | Solvent | Time | Coupling Reagent | Additive | Base | Amine (Equiv) | Amine Delay |
|---|---|---|---|---|---|---|---|
| 1 | 10% DMF/DCM | 68 h | DCC | DMAP | — | 5.0 | — |
| 2 | Dioxane | 68 h | DSC | — | — | 5.0 | 30 min |
| 3 | Dioxane | 92 h | DSC | — | — | 5.0 | 68 h |
| 4 | Dioxane | 68 h | — | — | — | 5.0 | — |
| 5 | Dioxane | 92 h | DSC | — | DIPEA | 5.0 | 68 h |
| 6 | 10% DMF/DCM | 68 h | MIBA | Mol. Sieve | — | 1.0 | — |
| 7 | 10% DMF/DCM | 68 h | DSC | — | — | 5.0 | 30 min |
| 8 | Dioxane | 18 h | DCC | — | — | 5.0 | — |
| 9 | Dioxane | 48 h | DSC | — | DIPEA | 5.0 | 24 h |
| 10 | 10% DMF/DCM | 18 h | DCC | — | — | 5.0 | — |
| 11 | DMF | 18 h | DCC | — | — | 5.0 | — |
| 12 | DMF | 48 h | DSC | — | DIPEA | 5.0 | 24 h |
| 13 | Dioxane | 48 h | DCC | DMAP | — | 10.0 | — |
| 14 | Dioxane | 48 h | DCC | — | — | 10.0 | — |
| 15 | Dioxane | 115 h | DSC | — | DIPEA | 5.0 | 91 h |
| 16 | Dioxane | 18 h | DSC | DMAP | DIPEA | 5.0 | 150 m |
| 17 | Dioxane | 115 h | DSC | DMAP | DIPEA | 5.0 | 91 h |
| 18 | Dioxane | 86 h | DSC | — | DIPEA | 7.5 | 68 h |
| 19 | DMF | 1 h | HATU | — | DIPEA | 1.2 | — |
| 20 | DMF | 1 h | PyBOP | — | DIPEA | 1.2 | — |
| 21 | 1:2 Dioxane:MeCN | 1 h | PyBOP | — | DIPEA | 1.2 | — |
| 22 | Dioxane | 18 h | DCC | HOBt | DIPEA | 1.2 | — |
| 23 | Dioxane | 18 h | DIC | HOBt | DIPEA | 1.2 | — |
| 24 | Dioxane | 18 h | EDC | HOBt | DIPEA | 1.2 | — |
| 25 | Dioxane | 48 h | DCC | NHS | DIPEA | 1.2 | 24 h |
| 26 | Dioxane | 48 h | DIC | NHS | DIPEA | 1.2 | 24 h |
| 27 | Dioxane | 48 h | EDC | NHS | DIPEA | 1.2 | 24 h |
| 28 | Dioxane | 48 h | DCC | PfpOH | DIPEA | 1.2 | 24 h |
| 29 | Dioxane | 48 h | DIC | PfpOH | DIPEA | 1.2 | 24 h |
| 30 | Dioxane | 48 h | EDC | PfpOH | DIPEA | 1.2 | 24 h |

DCC = N,N'-Dicyclohexylcarbodiimide
DIC = N,N'-Diisopropylcarbodiimide
DSC = N,N'-Disuccinimidyl carbonate
DIPEA = N,N-Diisopropylethylamine
DMF = N,N'-dimethylformamide
EDC = N-(3-Dimethylaminopropyl)-N'-ethylcarbodiimide hydrochloride
HATU = 1-[Bis(dimethylamino)methylene]-1H-1,2,3-triazolo[4,5-b]pyridinium 3-oxid hexafluorophosphate
HOBt = 1-Hydroxybenzotriazole hydrate
MIBA = 5-methoxy-2-iodophenylboronic acid
PyBOP = benzotriazol-1-yl-oxytripyrrolidinophosphonium hexafluorophosphate
PfpOH = 2,2,3,3,3-Pentafluoro-1-propanol In one aspect of the invention described herein, a prostacyclin compound of Formula (I), or a pharmaceutically acceptable salt thereof, is manufactured by a method described herein:

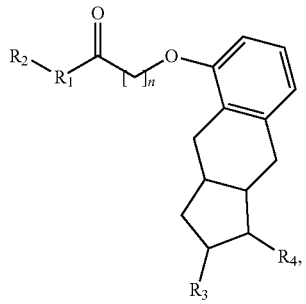

Formula (I)

wherein $R_1$ is NH, O or S;

$R_2$ is H, a linear $C_5$-$C_{18}$ alkyl, branched $C_5$-$C_{18}$ alkyl, linear $C_2$-$C_{18}$ alkenyl, branched $C_3$-$C_{18}$ alkenyl, aryl, aryl-$C_1$-$C_{18}$ alkyl; an amino acid or a peptide; $R_3$ is H, OH, optionally substituted linear or branched $C_1$-$C_{15}$ alkyoxy, O-optionally substituted linear or branched $C_2$-$C_{15}$ alkenyl, O—(C=O)-optionally substituted linear or branched $C_1$-$C_{15}$ alkyl, or O—(C=O)-optionally substituted linear or branched $C_2$-$C_{15}$ alkenyl;

$R_4$ is an optionally substituted linear or branched $C_1$-$C_{15}$ alkyl, or an optionally substituted linear or branched $C_2$-$C_{15}$ alkenyl; and n is an integer from 0 to 5, with the proviso that the prostacyclin compound of Formula (I) is not treprostinil.

In a further embodiment, a prostacyclin compound of Formula (I) is manufactured, wherein $R_3$ is OH and n is 0 or 1. In even a further embodiment, $R_4$ is an optionally substituted linear or branched $C_1$-$C_{15}$ alkyl. In even a further embodiment, $R_1$ is NH or O.

In one embodiment, a prostacyclin compound of Formula (I) is manufactured, wherein $R_1$ is NH, O or S; $R_2$ is a linear $C_5$-$C_{18}$ alkyl, branched $C_5$-$C_{18}$ alkyl, linear $C_2$-$C_{18}$ alkenyl, branched $C_3$-$C_{18}$ alkenyl; $R_3$ is H, OH or O-alkyl; $R_4$ is an optionally substituted linear or branched $C_1$-$C_{15}$ alkyl, or an optionally substituted linear or branched $C_2$-$C_{15}$ alkenyl; and n is an integer from 0 to 5. In even a further embodiment, $R_1$ is NH or O and $R_2$ is a linear $C_5$-$C_{18}$ alkyl or a branched $C_5$-$C_{18}$ alkyl.

In one embodiment, $R_2$ is aryl or aryl-$C_1$-$C_{18}$ alkyl; $R_3$ is OH and n is 0 or 1. In even a further embodiment, $R_4$ is an optionally substituted linear or branched $C_1$-$C_{15}$ alkyl.

In one embodiment, the present invention provides a method for manufacturing a prostacyclin compound of Formula (I), wherein the compound is a compound of one of Formulae (Ia), (Ib), (Ic) or (Id), or a pharmaceutically acceptable salt thereof:

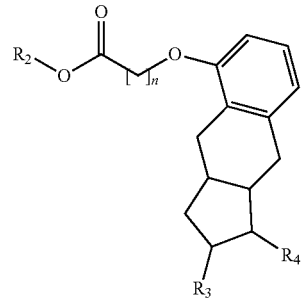

Formula (Ia)

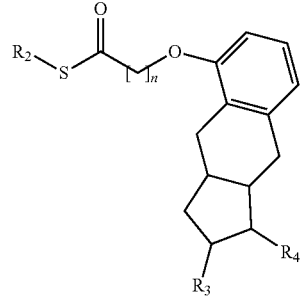

Formula (Ib)

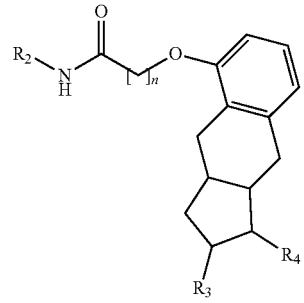

Formula (Ic)

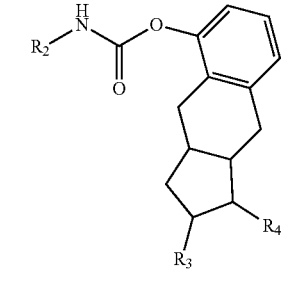

Formula (Id)

wherein, $R_2$ is H, a linear or branched $C_5$-$C_{18}$ alkyl, linear $C_2$-$C_{18}$ alkenyl, or a branched $C_3$-$C_{18}$ alkenyl;

$R_3$ is H, OH, optionally substituted linear or branched $C_1$-$C_{15}$ alkyoxy, O-optionally substituted linear or branched $C_2$-$C_{15}$ alkenyl, —O(C=O)-optionally substituted linear or branched $C_1$-$C_{15}$ alkyl, or —O(C=O)-optionally substituted linear or branched $C_2$-$C_{15}$ alkenyl; and $R_4$ is

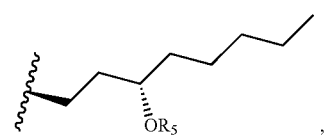

an optionally substituted linear or branched $C_1$-$C_{15}$ alkyl, or an optionally substituted linear or branched $C_2$-$C_{15}$ alkenyl, where $R_5$ is H, optionally substituted linear or branched $C_1$-$C_{15}$ alkyl, optionally substituted linear or branched $C_2$-$C_{15}$ alkenyl, (C=O)-optionally substituted linear or branched $C_1$-$C_{15}$ alkyl, or (C=O)-optionally substituted linear or branched $C_2$-$C_{15}$ alkenyl. In a further embodiment, $R_4$ is

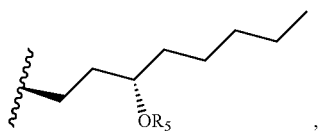

with the proviso that the compound is not treprostinil, i.e., $R_2$ and $R_5$ cannot both be H.

In one embodiment of Formula (Ia), Formula (Ib), Formula (Ic) and Formula (Id), $R_2$ is a linear or branched $C_5$-$C_{18}$ alkyl. In even a further embodiment, $R_2$ is

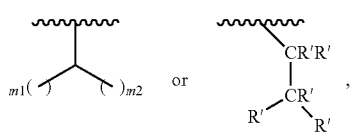

where m1 and m2 are each independently an integer selected from 1 to 9 and each occurrence of R' is independently H, a linear or branched $C_1$-$C_8$ alkyl, or a linear or branched $C_1$-$C_8$ alkenyl. In even a further embodiment, $R_2$ is

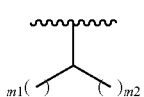

and m1 and m2 are both 4. In another embodiment, $R_2$ is

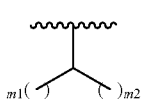

and m1 is 3 and m2 is 4, or m1 is 2 and m2 is 3.

When m1 and/or m2 is an integer from 2-9, the m1/m2 at the end of the carbon chain is $CH_3$, while the remaining m1/m2 groups are $CH_2$.

In one embodiment of Formula (Ia), Formula (Ib), Formula (Ic) and Formula (Id), $R_2$

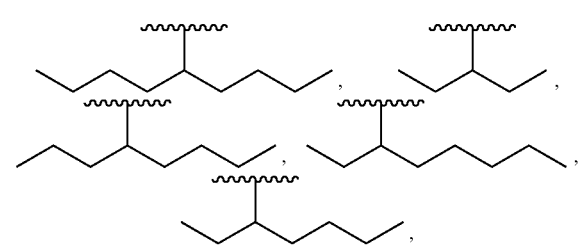

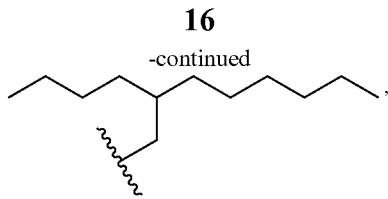

In a further embodiment, $R_3$ is OH and $R_4$ is

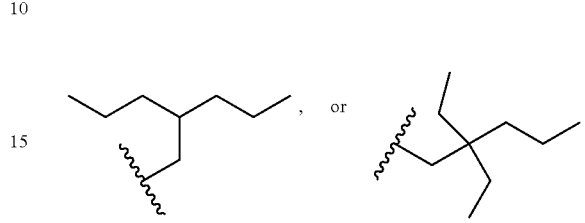

where $R_5$ is H, optionally substituted linear or branched $C_1$-$C_{15}$ alkyl, optionally substituted linear or branched $C_2$-$C_{15}$ alkenyl, (C=O)-optionally substituted linear or branched $C_1$-$C_{15}$ alkyl, or (C=O)-optionally substituted linear or branched $C_2$-$C_{15}$ alkenyl.

In one embodiment of Formulae (Ia), (Ib), (Ic) or (Id), $R_2$ is H, $R_3$ is OH and $R_4$ is

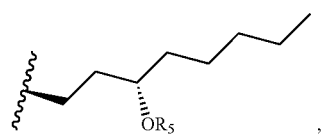

and $R_5$ is

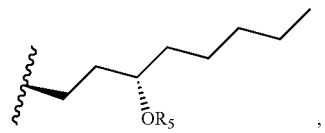

where m1 and m2 are each independently an integer selected from 1 to 9 and each occurrence of R' is independently H, a linear or branched $C_1$-$C_8$ alkyl, or a linear or branched $C_1$-$C_8$ alkenyl. When m1 and/or m2 is an integer from 2-9, the m1/m2 at the end of the carbon chain is $CH_3$, while the remaining m1/m2 groups are $CH_2$.

In another embodiment, a method for manufacturing a prostacyclin compound of one of Formula (Ia), (Ib), (Ic) or (Id) is provided wherein $R_3$ is OH, as provided in one of Formulae (Ia'), (Ib'), (Ic') or (Id'):

Formula (Ia')

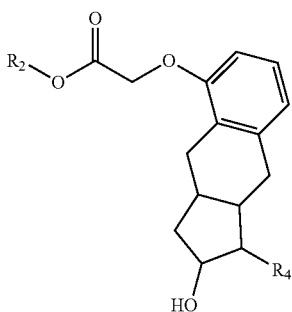

Formula (Ib')

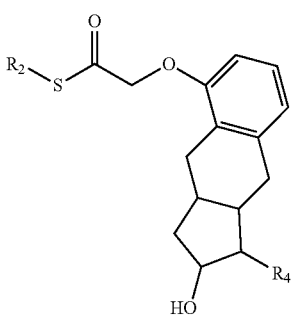

Formula (Ic')

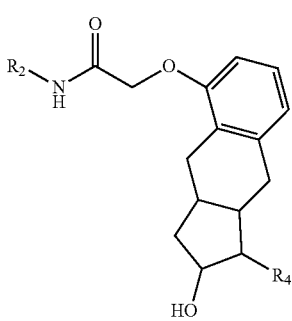

Formula (Id')

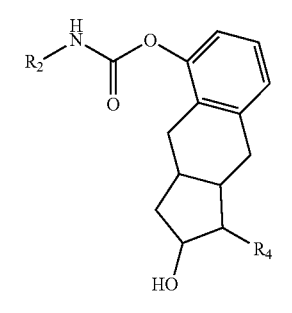

wherein, $R_2$ is H, a linear or branched $C_5$-$C_{18}$ alkyl, or a linear or branched $C_5$-$C_{18}$ alkenyl; and $R_4$ is

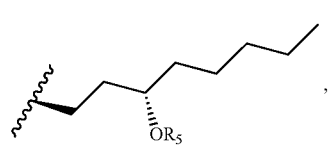

an optionally substituted linear or branched $C_1$-$C_{15}$ alkyl, or an optionally substituted linear or branched $C_2$-$C_{15}$ alkenyl, wherein $R_5$ is H, optionally substituted linear or branched $C_1$-$C_{15}$ alkyl, optionally substituted linear or branched $C_2$-$C_{15}$ alkenyl, (C=O)-optionally substituted linear or branched $C_1$-$C_{15}$ alkyl, or (C=O)-optionally substituted linear or branched $C_2$-$C_{15}$ alkenyl, with the proviso that $R_2$ and $R_5$ are not both H. In one embodiment of Formula (Ia'), Formula (Ib'), Formula (Ic') and Formula (Id'), $R_4$ is

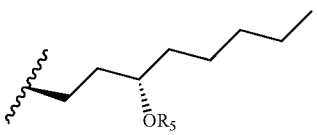

and $R_2$ is

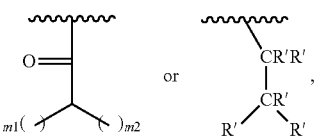

or $R_5$ is

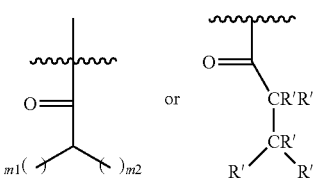

where m1 and m2 are each independently an integer selected from 1 to 9 and each occurrence of R' is independently H, a linear or branched $C_1$-$C_8$ alkyl, or a linear or branched $C_1$-$C_8$ alkenyl. In even a further embodiment, $R_2$ is

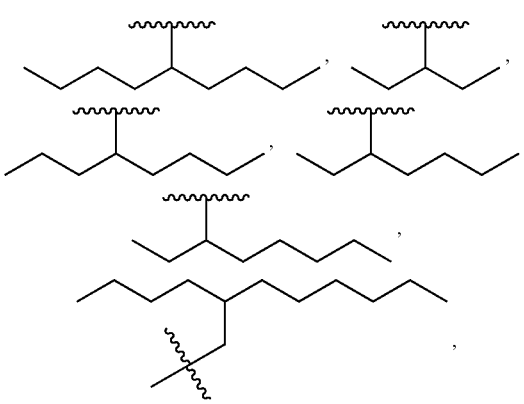

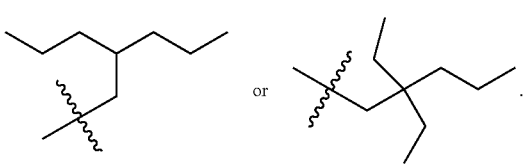

Yet another embodiment of the invention relates to a method for manufacturing a prostacyclin compound of one of Formula (Ia"), (Ib"), (Ic") or (Id"), or a pharmaceutically acceptable salt thereof:

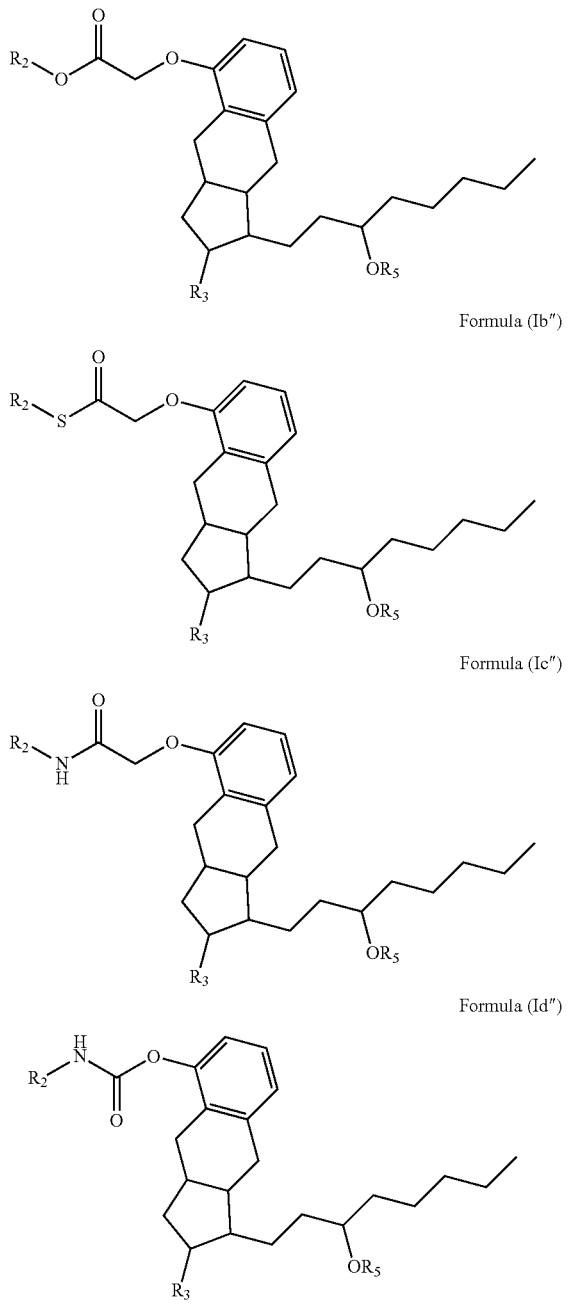

Formula (Ia″)

Formula (Ib″)

Formula (Ic″)

Formula (Id″)

wherein, $R_2$ is H, a linear or branched $C_5$-$C_{18}$ alkyl, linear $C_2$-$C_{18}$ alkenyl, branched $C_3$-$C_{18}$ alkenyl, aryl, aryl-$C_1$-$C_{18}$ alkyl; an amino acid or a peptide; and $R_3$ is H, OH, optionally substituted linear or branched $C_1$-$C_{15}$ alkyoxy, O-optionally substituted linear or branched $C_2$-$C_{15}$ alkenyl, O—(C=O)-optionally substituted linear or branched $C_1$-$C_{15}$ alkyl, or O—(C=O)-optionally substituted linear or branched $C_2$-$C_{15}$ alkenyl; and $R_5$ is H, optionally substituted linear or branched $C_1$-$C_{15}$ alkyl, optionally substituted linear or branched $C_2$-$C_{15}$ alkenyl, (C=O)-optionally substituted linear or branched $C_1$-$C_{15}$ alkyl, or (C=O)-optionally substituted linear or branched $C_2$-$C_{15}$ alkenyl, with the proviso that $R_2$ and $R_5$ are not both H. In a further embodiment, $R_3$ is OH and $R_2$ is 5-nonanyl, 4-heptyl, 4-octyl, 3-octyl, 2-dimethyl-1-propyl, 3,3-dimethyl-1-butyl, 2-ethyl-1-butyl, 3-pentyl, pentyl, hexyl, heptyl, octyl, nonyl, decyl, undecyl, dodecyl, tridecyl, tetradecyl, pentadecyl, hexadecyl, heptadecyl or octadecyl. In even a further embodiment, $R_2$ is decyl, undecyl, dodecyl, tridecyl, tetradecyl, pentadecyl, hexadecyl, heptadecyl or octadecyl. In even a further embodiment, $R_2$ is a linear alkyl.

One embodiment of the present invention is directed to a method for manufacturing a compound of Formula (Ic), (Ic′) and (Ic″). In a further embodiment, $R_2$ is a linear $C_5$-$C_{18}$ alkyl or a branched $C_5$-$C_{18}$ alkyl. In even a further embodiment, $R_2$ is a linear $C_6$-$C_{18}$ alkyl or a branched $C_6$-$C_{18}$ alkyl. In yet a further embodiment, $R_2$ is a linear $C_6$-$C_{14}$ alkyl, e.g., a linear $C_6$ alkyl, $C_8$ alkyl, $C_{10}$ alkyl, $C_{12}$ alkyl or $C_{14}$ alkyl.

In one embodiment, a compound of Formula (Ic″) is provided wherein $R_2$ is a linear $C_5$-$C_{18}$ alkyl; $R_3$ is OH and $R_5$ is H. In another embodiment, a compound of Formula (Ic″) is provided wherein $R_2$ is a linear $C_6$-$C_{18}$ alkyl; $R_3$ is OH and $R_5$ is H. In yet embodiment, a compound of Formula (Ic″) is provided wherein $R_2$ is a linear $C_6$-$C_{16}$ alkyl; $R_3$ is OH and $R_5$ is H. In even another embodiment, a compound of Formula (Ic″) is provided wherein $R_2$ is a linear $C_8$-$C_{14}$ alkyl; $R_3$ is OH and $R_5$ is OH.

In one embodiment, a method for manufacturing a prostacyclin compound of Formula (Ic″) is provided wherein $R_2$ is a linear $C_5$-$C_{18}$ alkyl; $R_3$ is OH and $R_5$ is H. In another embodiment, a compound of Formula (Ic″) is provided wherein $R_2$ is a branched $C_6$-$C_{18}$ alkyl; $R_3$ is OH and $R_5$ is H. In yet embodiment, a compound of Formula (Ic″) is provided wherein $R_2$ is a branched $C_6$-$C_{16}$ alkyl; $R_3$ is OH and $R_5$ is H. In even another embodiment, a compound of Formula (Ic″) is provided wherein $R_2$ is a branched $C_8$-$C_{14}$ alkyl; $R_3$ is OH and $R_5$ is H.

In yet another embodiment a method for manufacturing a prostacyclin compound of Formula (Ia″), (Ib″), (Ic″) or (Id″) is provided, wherein $R_3$ is OH, $R_5$ is H and $R_2$ is

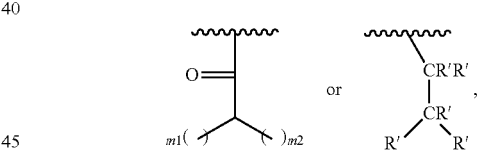

and m1 and m2 are each independently an integer selected from 1 to 9. In even a further embodiment, $R_2$ is

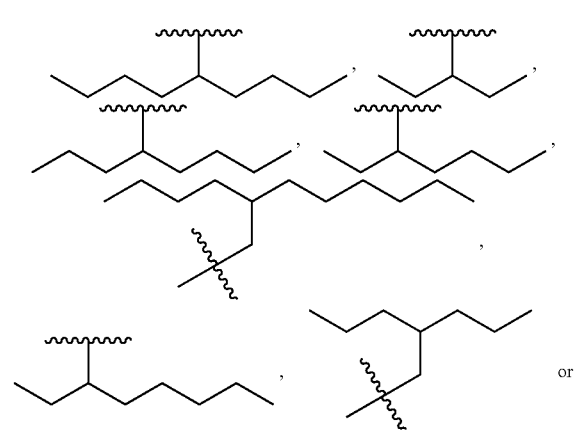

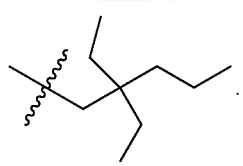

In yet another embodiment of Formula (Ia"), (Ib"), (Ic") or (Id"), $R_2$ is H, $R_3$ is OH, and $R_5$ is

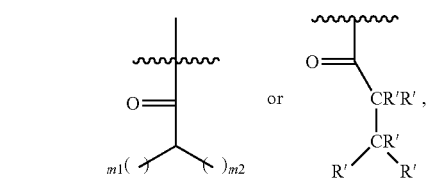

where m1 and m2 are each independently an integer selected from 1 to 9. In even a further embodiment, $R_2$ is

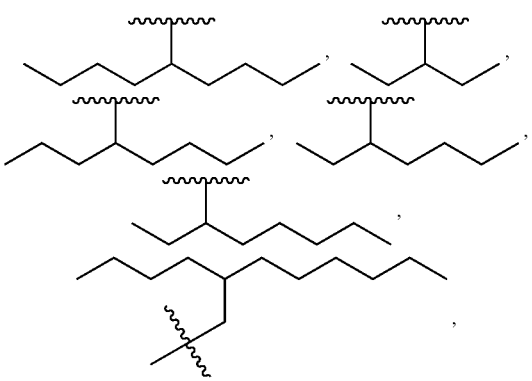

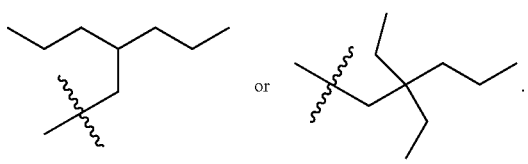

or

In one embodiment, a method for manufacturing a prostacyclin compound of Formula (I), (Ia), (Ib), (Ic) or (Id) is provided where $R_2$ is a linear or branched $C_5$-$C_{18}$ alkyl. In a further embodiment, $R_2$ is 5-nonanyl, 4-heptanyl, 4-octanyl, 3-octanyl, 2-dimethyl-1-propanyl, 3,3-dimethyl-1-butanyl, 2-ethyl-1-butanyl, 3-pentanyl, pentyl, hexyl, heptyl, octyl, nonyl, decyl, undecyl, dodecyl, tridecyl, tetradecyl, pentadecyl, hexadecyl, heptadecyl or octadecyl.

In one embodiment, a method for manufacturing a prostacyclin compound of Formula (I), (Ia), (Ib), (Ic), (Id), (Ia'), (Ib'), (Ic'), (Id'), (Ia"), (Ib"), (Ic") or (Id") is provided where $R_2$ is a linear or branched $C_5$-$C_{18}$ alkyl. In even a further embodiment, $R_2$ is a linear $C_5$-$C_{18}$ alkyl. In another embodiment, $R_2$ is

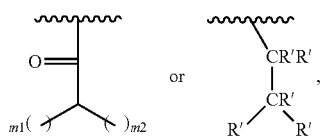

where m1 and m2 are each independently an integer selected from 1 to 9 and each occurrence of R' is independently H, a linear or branched $C_1$-$C_8$ alkyl, or a linear or branched $C_1$-$C_8$ alkenyl. In even a further embodiment, $R_2$ is

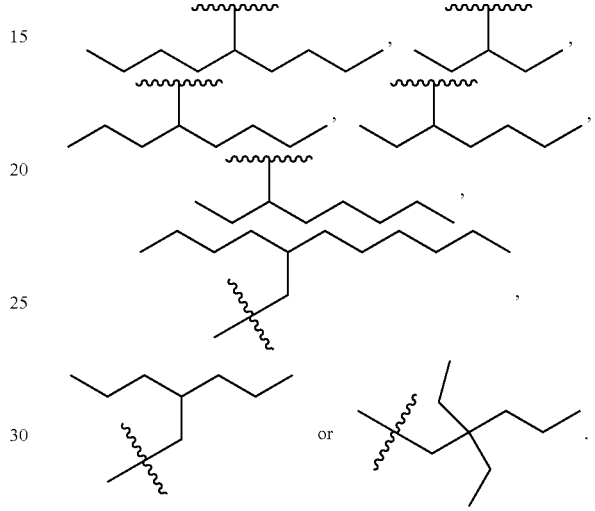

In another embodiment, a method for manufacturing a prostacyclin compound of Formula (I), (Ia), (Ib), (Ic) or (Id) is provided wherein $R_2$ is a branched $C_5$-$C_{18}$ alkyl. In a further embodiment, $R_2$ is 5-nonanyl, 4-heptyl, 4-octyl, 3-octyl, 2-dimethyl-1-propyl, 3,3-dimethyl-1-butyl, 2-ethyl-1-butyl, 3-pentyl, pentyl, hexyl, heptyl, octyl, nonyl, decyl, undecyl, dodecyl, tridecyl, tetradecyl, pentadecyl, hexadecyl, heptadecyl or octadecyl.

In one embodiment of the invention, the prostacyclin compound manufactured by the methods provided herein has the following structure:

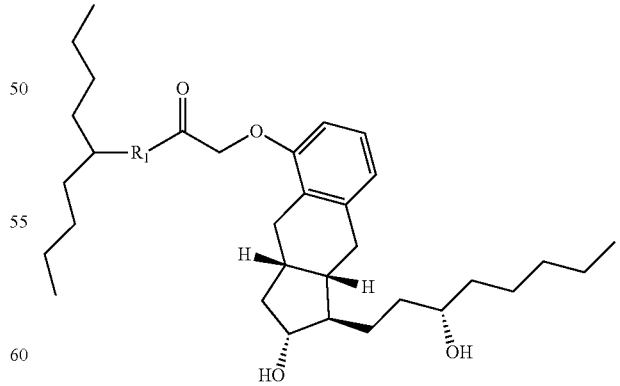

wherein $R_1$ is NH, O or S.

For example, $R_1$ is O or N, and one of the following compounds (5-nonanyl treprostinil (alkyl ester, 5C$_9$-TR) or 5-nonanyl treprostinil (amide linked; 5C9-TR-A), is provided:

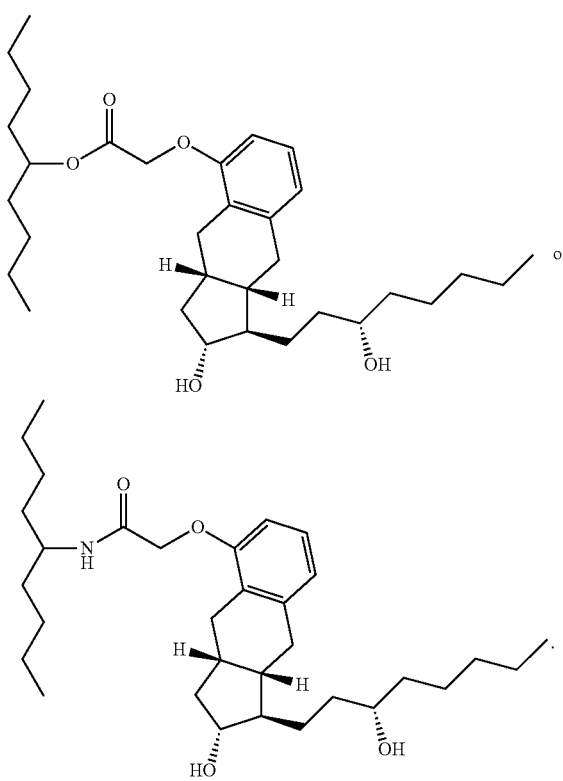

In one embodiment, a method for manufacturing a prostacyclin compound of Formula (I), (Ia), (Ib), (Ic) or (Id) is provided wherein $R_2$ is

where m1 and m2 are each independently each an integer selected from 1 to 9 and each occurrence of R' is independently H, a linear or branched $C_1$-$C_8$ alkyl, or a linear or branched $C_1$-$C_8$ alkenyl.

When m1 and/or m2 is an integer from 2-9, the m1/m2 at the end of the carbon chain is $CH_3$, while the remaining m1/m2 groups are $CH_2$.

In even another embodiment, a method for manufacturing a prostacyclin compound of Formula (I), (Ia), (Ib), (Ic), (Id), (Ia'), (Ib'), (Ic'), (Id'), (Ia"), (Ib"), (Ic") or (Id") is provided and $R_2$ is

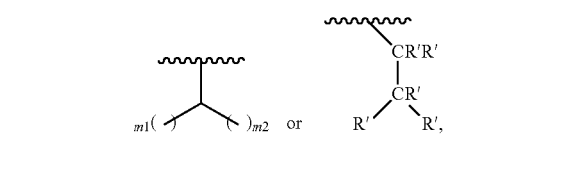

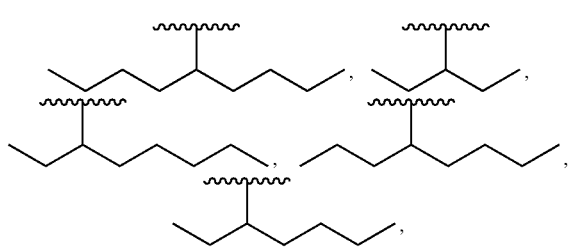

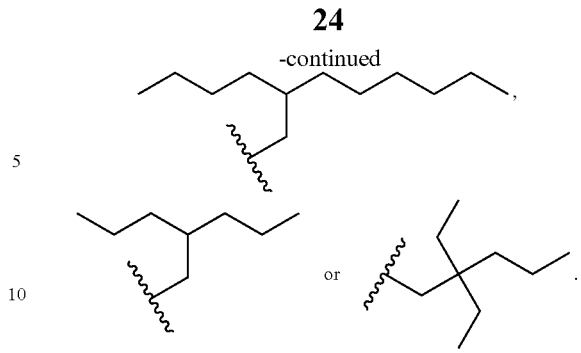

The compounds provided herein can include a symmetrical branched alkyl or an asymmetrical branched alkyl as the $R_2$ moiety. For example, where $R_2$ is

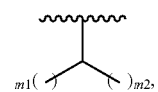

m1 and m2 can be the same integer and $R_2$ is therefore a symmetrical branched alkyl. $R_2$ is an assymetrical branched alkyl when m1 and m2 are different.

In another embodiment, a compound of Formula (I), (Ia), (Ib), (Ic), (Id), (Ia'), (Ib'), (Ic'), (Id'), (Ia"), (Ib"), (Ic") or (Id") is provided, $R_2$ is

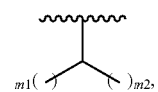

m1 is 2 and m2 is 3, m1 and m2 are each independently 4, or m1 and m2 are each independently 3 is provided via one of the methods described herein.

In another embodiment, the prostacyclin compound manufactured by the disclosed methods comprises an asymmetrical branched alkyl at the $R_2$ position, such as, for example, 3-hexanyl ($3C_6$), 2-heptanyl ($2C_7$), 3-heptanyl ($3C_7$), 2-octanyl ($2C_8$), 3-octanyl ($3C_8$), or 4-octanyl ($4C_8$).

In another embodiment, a prostacyclin compound of Formula (I), (Ia), (Ib), (Ic) or (Id) is manufactured by the disclosed methods, wherein $R_2$ is a branched alkyl selected from 2,2-diethyl-1-pentyl, 3-pentyl, 4-octyl, 5-nonanyl, 2-ethyl-1-butyl, 2-propyl-1-pentyl, 12-butyl-1-octyl, 2-dimethyl-1-propyl, and 3,3-dimethyl-1-butyl.

In yet another embodiment, a method for manufacturing a prostacyclin compound of Formula (I), (Ia), (Ib), (Ic), (Id), (Ia'), (Ib'), (Ic') or (Id') is provided, wherein, $R_2$ is a linear or branched $C_5$-$C_{18}$ alkenyl. For example, in one embodiment, $R_2$ is a linear $C_5$-$C_{18}$ alkenyl selected from pentenyl, hexenyl, heptenyl, octenyl, nonenyl, decenyl, undecenyl, tridecenyl, tetradecenyl, pentadecenyl, hexadecenyl, heptadecenyl or octadecenyl. In a further embodiment, $R_3$ is OH. In another embodiment, $R_2$ is a branched $C_5$-$C_{18}$ alkenyl selected from pentenyl, hexenyl, heptenyl, octenyl, nonenyl, decenyl, undecenyl, tridecenyl, tetradecenyl, pentadecenyl, hexadecenyl, heptadecenyl or octadecenyl. In a further embodiment, $R_3$ is OH.

In one embodiment, a prostacyclin compound of Formula (I), (Ia), (Ib), (Ic) or (Id) is provided and $R_4$ is

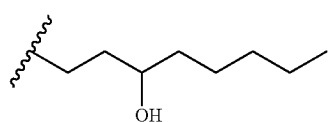 [SMILES: *CCC(O)CCCCC]

is synthesized by one of the methods provided herein. In a further embodiment, $R_4$ is

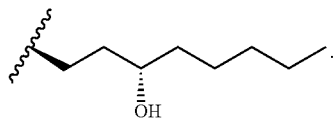

In one embodiment, a prostacyclin compound of Formula (I), (Ia), (Ib), (Ic) or (Id) is is synthesized by one of the methods provided herein and $R_2$ a linear $C_5$-$C_{18}$ alkyl, $R_3$ is OH and $R_4$ is

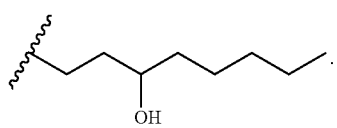 [SMILES: *CCC(O)CCCCC]

In a further embodiment, $R_2$ is 5-nonanyl, 4-heptyl, 4-octanyl, 3-octanyl, 2-dimethyl-1-propyl, 3,3-dimethyl-1-butyl, 2-ethyl-1-butyl, 3-pentyl, pentyl, hexyl, heptyl, octyl, nonyl, decyl, undecyl, dodecyl, tridecyl, tetradecyl, pentadecyl, hexadecyl, heptadecyl or octadecyl.

In one embodiment, a prostacyclin compound of Formula (I), (Ia), (Ib), (Ic) or (Id) is is synthesized by one of the methods provided herein and $R_2$ hexyl, dodecyl, tetradecyl, hexadecyl, 5-nonanyl, 4-heptanyl, 4-octanyl, 3-octanyl, 2-dimethyl-1-propyl, 3,3-dimethyl-1-butyl, 2-ethyl-1-butyl, 3-pentyl, $R_3$ is OH and $R_4$ is

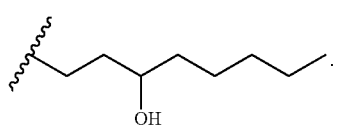 [SMILES: *CCC(O)CCCCC]

In one embodiment, a prostacyclin compound of Formula (I), (Ia), (Ib), (Ic) or (Id) is is synthesized by one of the methods provided herein and $R_2$ hexyl, $R_3$ is OH and $R_4$ is

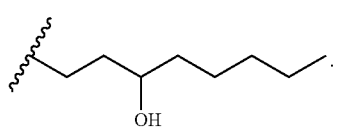 [SMILES: *CCC(O)CCCCC]

In one embodiment, a prostacyclin compound of Formula (I), (Ia), (Ib), (Ic) or (Id) is is synthesized by one of the methods described herein and $R_2$ hexyl, $R_3$ is OH and $R_4$ is

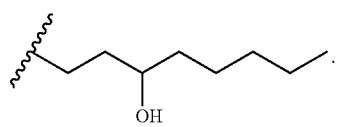 [SMILES: *CCC(O)CCCCC]

In another embodiment, a method for manufacturing a prostacyclin compound of Formula (Ia"), (Ib"), (Ic") or (Id") is provided and $R_2$ hexyl, $R_3$ is OH $R_4$ is H. In a further embodiment, the prostacyclin compound is a compound of Formula (Ic"). In yet another embodiment, a prostacyclin compound of Formula (Ia"), (Ib"), (Ic") or (Id") is provided and $R_2$ dodecyl, tetradecyl, pentadecyl or hexadecyl, $R_3$ is OH $R_4$ is H. In a further embodiment, the compound is a compound of Formula (Ia"). In even a further embodiment, the compound is present in a lipid nanoparticle formulation as described in more detail below.

In one embodiment, a prostacyclin compound of Formula (I), (Ia), (Ib), (Ic) or (Id), or pharmaceutically acceptable salt, is synthesized by a method described herein, and $R_2$ heptyl, $R_3$ is OH and $R_4$ is

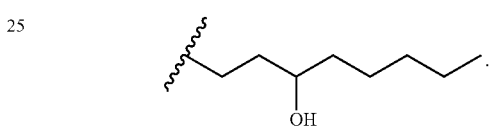

In one embodiment, a prostacyclin compound of Formula (I), (Ia), (Ib), (Ic) or (Id), or pharmaceutically acceptable salt, is synthesized by a method described herein, and $R_2$ octyl, $R_3$ is OH and $R_4$ is

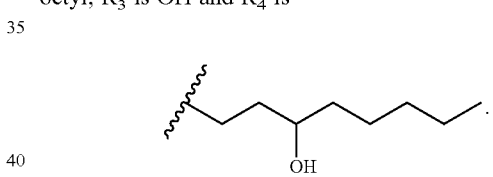

In one embodiment, a prostacyclin compound of Formula (I), (Ia), (Ib), (Ic) or (Id), or pharmaceutically acceptable salt, is synthesized by a method described herein, and $R_2$ nonyl, $R_3$ is OH and $R_4$ is

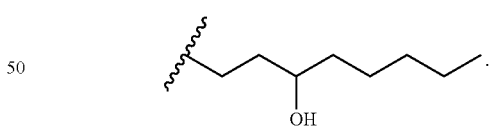

In another embodiment, a prostacyclin compound of Formula (I), (Ia), (Ib), (Ic) or (Id), or pharmaceutically acceptable salt, is synthesized by a method described herein, and $R_2$ decyl, $R_3$ is OH and $R_4$ is

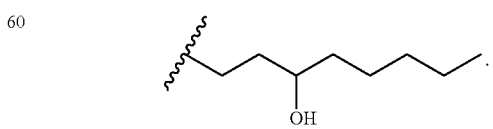

In yet another embodiment, a prostacyclin compound of Formula (I), (Ia), (Ib), (Ic) or (Id), or pharmaceutically acceptable salt, is synthesized by a method described herein, and $R_2$ undecyl, $R_3$ is OH and $R_4$ is

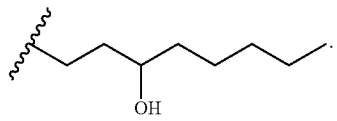 [SMILES: *CCC(O)CCCCC]

In even another embodiment, a prostacyclin compound of Formula (I), (Ia), (Ib), (Ic) or (Id), or pharmaceutically acceptable salt, is synthesized by a method described herein, and $R_2$ dodecyl, $R_3$ is OH and $R_4$ is

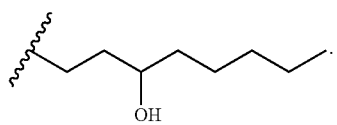 [SMILES: *CCC(O)CCCCC]

In one embodiment, a prostacyclin compound of Formula (I), (Ia), (Ib), (Ic) or (Id), or pharmaceutically acceptable salt, is synthesized by a method described herein, and $R_2$ tridecyl, $R_3$ is OH and $R_4$ is

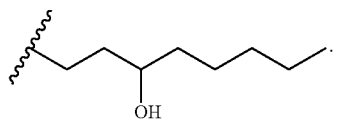 [SMILES: *CCC(O)CCCCC]

In another embodiment, a prostacyclin compound of Formula (I), (Ia), (Ib), (Ic), or (Id), or pharmaceutically acceptable salt, is synthesized by a method described herein, and $R_2$ tetradecyl, $R_3$ is OH and $R_4$ is

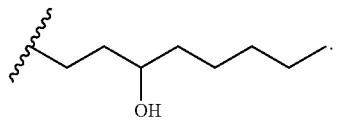 [SMILES: *CCC(O)CCCCC]

In even another embodiment, a prostacyclin compound of Formula (I), (Ia), (Ib), (Ic) or (Id), or pharmaceutically acceptable salt, is synthesized by a method described herein, and $R_2$ pentadecyl, $R_3$ is OH and $R_4$ is

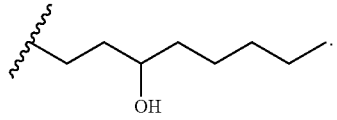 [SMILES: *CCC(O)CCCCC]

Another embodiment of the invention concerns a prostacyclin compound of Formula (I), (Ia), (Ib), (Ic) or (Id), or pharmaceutically acceptable salt is synthesized by a method described herein, wherein $R_2$ hexadecyl, $R_3$ is OH and $R_4$ is

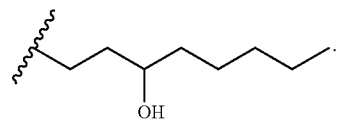

Yet another embodiment of the invention concerns a prostacyclin compound of Formula (I), (Ia), (Ib), (Ic) or (Id), a or pharmaceutically acceptable salt is synthesized by a method described herein, wherein $R_2$ heptadecyl, $R_3$ is OH and $R_4$ is

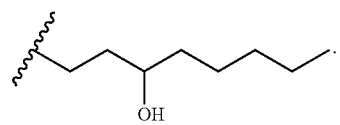 [SMILES: *CCC(O)CCCCC]

Yet another embodiment of the invention concerns a prostacyclin compound of Formula (I), (Ia), (Ib), (Ic) or (Id), or a pharmaceutically acceptable salt is synthesized by a method described herein, wherein $R_2$ octadecyl, $R_3$ is OH and $R_4$ is

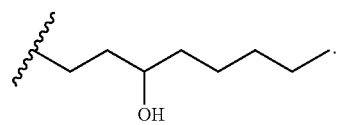 [SMILES: *CCC(O)CCCCC]

In one embodiment, a method is provided for manufacturing a compound of Formula (I), (Ia), (Ib), (Ic) or (Id), or a pharmaceutically acceptable salt, wherein one or more hydrogen atoms is substituted with a deuterium. Accordingly, in one embodiment, the present invention relates to an isotopologue of Formula (I), (Ia), (Ib), (Ic) or (Id), substituted with one or more deuterium atoms. The isotopologue of Formula (I), (Ia), (Ib), (Ic) or (Id) may be used to accurately determine the concentration of compounds of Formula (I), (Ia), (Ib), (Ic) or (Id) in biological fluids and to determine metabolic patterns of compounds of Formula (I), (Ia), (Ib), (Ic) or (Id) and its isotopologues.

In another embodiment of the invention, a method for manufacturing a prostacyclin compound of Formula (II), or a pharmaceutically acceptable salt thereof, is provided:

Formula (II)

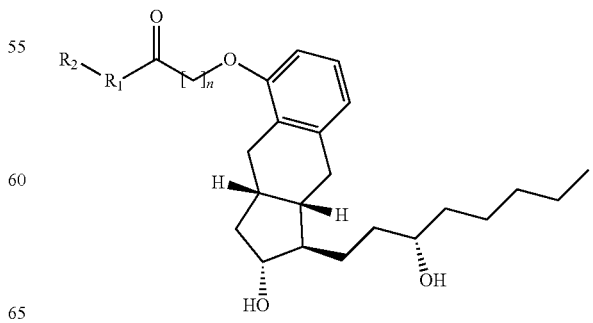

wherein $R_1$ is NH, O or S;

$R_2$ is a linear or branched $C_5$-$C_{18}$ alkyl, a linear $C_2$-$C_{18}$ alkenyl or a branched $C_3$-$C_{18}$ alkenyl, aryl, aryl-$C_1$-$C_{18}$ alkyl, an amino acid or a peptide; and n is an integer from 0 to 5.

In one embodiment, the method comprises manufacturing a prostacyclin compound of Formula (II), or a pharmaceutically acceptable salt thereof, wherein $R_1$ is NH, O or S; $R_2$ is a linear or branched $C_5$-$C_{18}$ alkyl, a linear $C_2$-$C_{18}$ alkenyl or a branched $C_3$-$C_{18}$ alkenyl; and n is an integer from 0 to 5. In a further embodiment, n is 1 and $R_1$ is NH or O.

In one embodiment, the method comprises manufacturing a prostacyclin compound of Formula (II), wherein the prostacyclin compound is a compound of formula (IIa), (IIb), (IIc) or (IId), or a pharmaceutically acceptable salt thereof:

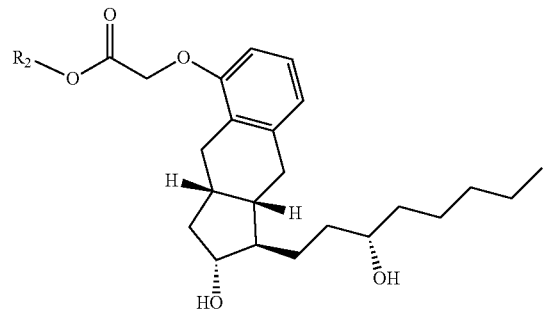

Formula (IIa)

Formula (IIb)

Formula (IIc)

Formula (IId)

wherein $R_2$ is a linear or branched $C_5$-$C_{18}$ alkyl, a linear $C_2$-$C_{18}$ alkenyl or a branched $C_3$-$C_{18}$ alkenyl, aryl, aryl-$C_1$-$C_{18}$ alkyl, an amino acid or a peptide. In a further embodiment, a compound of formula (IIa), (IIb), (IIc) or (IId) is provided wherein $R_2$ is a linear or branched $C_5$-$C_{18}$ alkyl, a linear $C_2$-$C_{18}$ alkenyl or a branched $C_3$-$C_{18}$ alkenyl. In one embodiment, a compound of Formula (II), (IIa), (IIb), (IIc) or (IId) is provided, wherein one or more hydrogen atoms is substituted with a deuterium. Accordingly, in one embodiment, the present invention relates to an isotopologue of Formula (II), (IIa), (IIb), (IIc) or (IId), substituted with one or more deuterium atoms. The isotopologue of Formula (II), (IIa), (IIb), (IIc) or (IId) may be used to accurately determine the concentration of compounds of Formula (II), (IIa), (IIb), (IIc) or (IId) in biological fluids and to determine metabolic patterns of compounds of Formula (II), (IIa), (IIb), (IIc) or (IId) and its isotopologues. The invention further provides compositions comprising these deuterated isotopologues and methods of treating diseases and conditions, as set forth herein.

In another embodiment, the method comprises manufacturing a prostacyclin compound of Formula (IIc). In a further embodiment, $R_2$ is a linear $C_5$-$C_{18}$ alkyl or a branched $C_5$-$C_{18}$ alkyl. For example, in one embodiment, $R_2$ is a linear $C_6$-$C_{18}$ alkyl. In another embodiment of Formula (IIc), $R_2$ is a linear $C_6$-$C_{10}$ alkyl. In even a further embodiment of Formula (IIc), $R_2$ is a hexyl, heptyl or octyl.

Compounds of Formula (IIa) and Formula (IId) that can be manufactured by the methods described herein are provided in tables 3 and 4 below.

TABLE 3

Compounds of Formula (IIa)

| | | | |
|---|---|---|---|
| $R_2$= linear $C_5$-$C_{18}$ alkyl | $R_2$= branched $C_5$-$C_{18}$ alkyl | $R_2$= linear $C_8$ alkyl | $R_2$= branched $C_6$ alkyl |
| $R_2$= linear $C_6$-$C_{18}$ alkyl | $R_2$= branched $C_6$-$C_{18}$ alkyl | $R_2$= linear $C_9$ alkyl | $R_2$= branched $C_7$ alkyl |
| $R_2$= linear $C_7$-$C_{18}$ alkyl | $R_2$= branched $C_7$-$C_{18}$ alkyl | $R_2$= linear $C_{10}$ alkyl | $R_2$= branched $C_8$ alkyl |
| $R_2$= linear $C_8$-$C_{18}$ alkyl | $R_2$= branched $C_8$-$C_{18}$ alkyl | $R_2$= linear $C_{11}$ alkyl | $R_2$= branched $C_9$ alkyl |
| $R_2$= linear $C_9$-$C_{18}$ alkyl | $R_2$= branched $C_9$-$C_{18}$ alkyl | $R_2$= linear $C_{12}$ alkyl | $R_2$= branched $C_{10}$ alkyl |
| $R_2$= linear $C_{10}$-$C_{18}$ alkyl | $R_2$= branched $C_{10}$-$C_{18}$ alkyl | $R_2$= linear $C_{13}$ alkyl | $R_2$= branched $C_{11}$ alkyl |

TABLE 3-continued

Compounds of Formula (IIa)

| | | | |
|---|---|---|---|
| $R_2$- linear $C_{11}$-$C_{18}$ alkyl | $R_2$- branched $C_{11}$-$C_{18}$ alkyl | $R_2$- linear $C_{14}$ alkyl | $R_2$- branched $C_{12}$ alkyl |
| $R_2$- linear $C_{12}$-$C_{18}$ alkyl | $R_2$- branched $C_{12}$-$C_{18}$ alkyl | $R_2$- linear $C_{15}$ alkyl | $R_2$- branched $C_{13}$ alkyl |

TABLE 4

Compounds of Formula (IIc)

| | | | |
|---|---|---|---|
| $R_2$- linear $C_5$-$C_{18}$ alkyl | $R_2$- branched $C_5$-$C_{18}$ alkyl | $R_2$- linear $C_6$ alkyl | $R_2$- branched $C_6$ alkyl |
| $R_2$- linear $C_6$-$C_{18}$ alkyl | $R_2$- branched $C_6$-$C_{18}$ alkyl | $R_2$- linear $C_7$ alkyl | $R_2$- branched $C_7$ alkyl |
| $R_2$- linear $C_7$-$C_{18}$ alkyl | $R_2$- branched $C_7$-$C_{18}$ alkyl | $R_2$- linear $C_8$ alkyl | $R_2$- branched $C_8$ alkyl |
| $R_2$- linear $C_8$-$C_{18}$ alkyl | $R_2$- branched $C_8$-$C_{18}$ alkyl | $R_2$- linear $C_9$ alkyl | $R_2$- branched $C_9$ alkyl |
| $R_2$- linear $C_9$-$C_{18}$ alkyl | $R_2$- branched $C_9$-$C_{18}$ alkyl | $R_2$- linear $C_{10}$ alkyl | $R_2$- branched $C_{10}$ alkyl |
| $R_2$- linear $C_{10}$-$C_{18}$ alkyl | $R_2$- branched $C_{10}$-$C_{18}$ alkyl | $R_2$- linear $C_{11}$ alkyl | $R_2$- branched $C_{11}$ alkyl |
| $R_2$- linear $C_5$-$C_{12}$ alkyl | $R_2$- branched $C_5$-$C_{12}$ alkyl | $R_2$- linear $C_{12}$ alkyl | $R_2$- branched $C_{12}$ alkyl |
| $R_2$- linear $C_6$-$C_{10}$ alkyl | $R_2$- branched $C_6$-$C_{10}$ alkyl | $R_2$- linear $C_{13}$ alkyl | $R_2$- branched $C_{13}$ alkyl |

Yet another embodiment of the invention relates to a method for manufacturing a prostacyclin compound of Formula (III), or a pharmaceutically acceptable salt thereof:

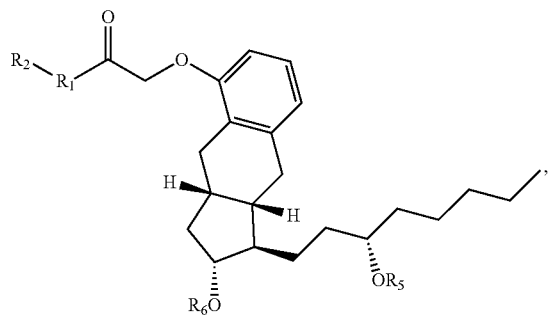

Formula (III)

wherein $R_1$ and $R_2$ are defined as provided for Formula (I) and (II), and $R_5$ and $R_6$ are independently selected from H, optionally substituted linear or branched $C_1$-$C_{15}$ alkyl, optionally substituted linear or branched $C_2$-$C_{15}$ alkenyl, (C=O)-optionally substituted linear or branched $C_1$-$C_{15}$ alkyl, or (C=O)-optionally substituted linear or branched $C_2$-$C_{15}$ alkenyl, with the proviso that the prostacyclin compound of Formula (III) is not treprostinil.

In one embodiment, the manufacturing methods provide prostacyclin compounds that contain a chiral moiety at one or more of the $R_2$, $R_5$ and/or $R_6$ positions. For example, the moiety at position $R_2$, in one embodiment, is a chiral moiety and comprises either the R isomer, the S isomer, or a mixture thereof. An optical isomer at position $R_2$, $R_5$ and/or $R_6$ can also be classified with the D/L nomenclature. For example, where $R_2$ is an amino acid or an amino acid moiety, the amino acid or amino acid moiety can be the D-isomer, L-isomer, or a mixture thereof.

In one embodiment, one or more of the $R_2$, $R_5$ and/or $R_6$ moieties is the R isomer or S isomer. In another embodiment, one or more of the $R_2$, $R_5$ and/or $R_6$ moieties provided herein comprise a mixture of R and S moieties. The "R isomer" or "S isomer" as used herein refers to an enantiomerically pure isomer. An "enantiomerically pure isomer" has at least 90%, at least 95%, at least 96%, at least 97%, at least 98%, or at least 99% pure R- or S-isomer or when using the D/L nomenclature, D- or L-isomer. A racemic compound is a compound having a mixture in equal amounts of both enantiomers.

EXAMPLES

The present invention is further illustrated by reference to the following Examples. However, it should be noted that these Examples, like the embodiments described above, are illustrative and are not to be construed as restricting the scope of the invention in any way.

Example 1—Synthesis of Treprostinil Alkyl Esters

Treprostinil compounds derivatized with alkyl groups at the carboxylic acid moiety were prepared. Specifically, treprostinil was derivatized at the carboxylic acid moiety with $C_2$, $C_3$, $C_4$, $C_5$, $C_6$, $C_8$, $C_{10}$, $C_{12}$, $C_{16}$, and $C_{18}$ alkyl chains (i.e., $R_2$ in Formula (A), below, is $C_2$, $C_3$, $C_4$, $C_5$, $C_6$, $C_8$, $C_{10}$, $C_{12}$, $C_{16}$ or $C_{18}$ alkyl) to make treprostinil alkyl esters of various ester chain lengths. Treprostinil can be synthesized, for example, by the methods disclosed in U.S. Pat. Nos. 6,765,117 and 8,497,393. Synthesis of prostaglandin derivatives is described in U.S. Pat. No. 4,668,814. The disclosures of U.S. Pat. Nos. 6,765,117; 8,497,393 and 4,668,814 are each incorporated by reference in their entireties for all purposes.

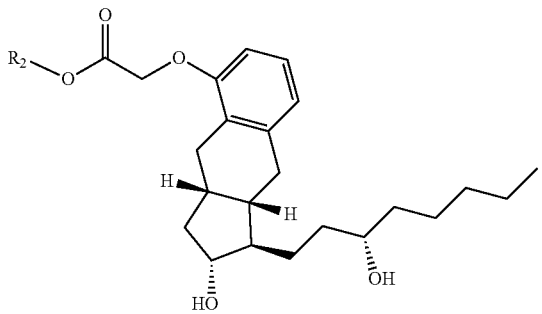

Formula (A)

Scheme 1:

Treprostinil esterification was catalyzed by strongly acidic resin Amberlyst® 15 (Rohm and Haas). Treprostinil acid was dissolved in anhydrous dioxane/alcohol at a concentration 10 mg/mL (typically 4 mL). Alcohol ($R_2$—OH) added was appropriate to make corresponding chain length at the $R_2$ group. By way of example, for the $C_2$ (ethyl ester) compound, the alcohol was ethanol. The molar amount of alcohol in the solvent was ten times the molar amount of treprostinil.

Treprostinil in dioxane/alcohol solution was added to washed and dry Amberlyst resin. Per each 40 mg treprostinil, 1 g resin in a glass vial was added. The mixture was placed on a shaker and incubated overnight at 40° C. Next, the liquid portion was taken out of the vial, washed twice with 3 mL dioxane. All recovered solvent was then collected. The solvent was dried by nitrogen stream until the evaporation stopped. The remaining treprostinil alkyl ester and nonvolatile alcohol (if long chain alcohol used) was dissolved in 2 mL hexane/ethyl acetate 1:1, and cleaned by liquid-liquid extraction vs. equal volume of phosphate buffer, and then water. Next, the organic layer was separated and dried by nitrogen stream and further in vacuum. If a long chain alcohol used, an additional purification step was required to separate alcohol by liquid chromatography. ACE CN, 5 μm, Ultra-Inert HPLC Column, 100×21.2 mm was used, with mobile phase of hexane/propanol 98:2%.

Scheme 2:

To a solution of (1R,2R,3aS,9aS)-[[2,3,3a,4,9,9a-hexahydro-2-hydroxy-1-[(3S)-3-hydroxyoctyl]-1H-benz[f]inden-5-yl]oxy]acetic acid (treprostinil) (78.1 mg, 200 μmoles) dissolved in 1,4-dioxane (2.0 mL) was added Amberlyst® 15 resin (2.0 g) and alcohol $R_2$—OH (2.0 mmoles, 10 equivalents). The reaction mixture was heated to 40° C. and allowed to shake at approximately 100 rpm for 18-196 hours. Solvent was removed and the resin was washed with acetonitrile (MeCN) (3×3 mL). The 1,4-dioxane and MeCN extracts were combined and dried using a gentle stream of warmed $N_2$ gas and gentle heat to yield a thick waxy solid. The crude material was dissolved in 20% "PrOH/Hexanes and submitted to preparatory HPLC purification. Solvent was removed from the purified material using a gentle stream of warmed $N_2$ gas and gentle heat to yield an off-white waxy solid. The pure material was suspended in ethyl lactate for storage and was submitted to analytical HPLC for concentration determination.

By way of example, the following compounds of Formula (A), set forth in Table 5 were synthesized by the method of scheme 2.

TABLE 5

| $R_2$ group | Compound abbreviation |
|---|---|
| 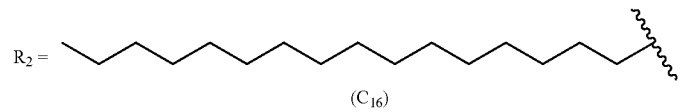 [SMILES: *CCCCCCCCCCCCCCCC ; "(C16)"] ($C_{16}$) | $C_{16}$-TR |
| 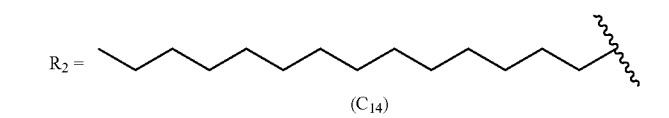 ($C_{14}$) | $C_{14}$-TR |
| 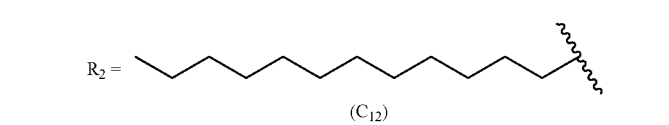 ($C_{12}$) | $C_{12}$-TR |
| 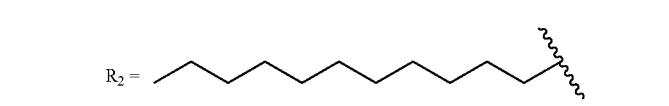 ($C_{11}$) | $C_{11}$-TR |
| 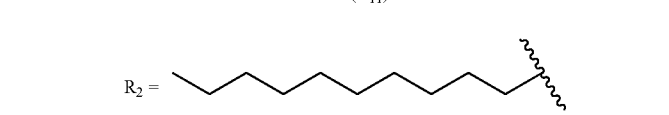 ($C_{10}$) | $C_{10}$-TR |
| 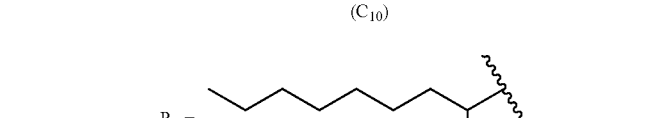 ($2C_9$) | $C_9$-TR |
| 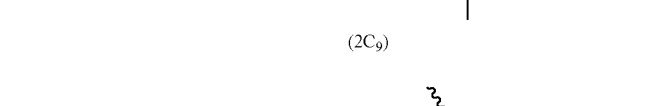 ($5C_9$) | $5C_9$-TR |

TABLE 5-continued
| R$_2$ group | Compound abbreviation |
|---|---|
| 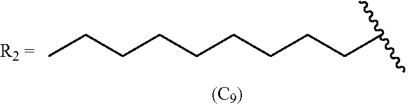 R$_2$ = (C$_9$) | 2C$_9$-TR |
| 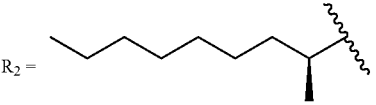 R$_2$ = ((S)-2C$_9$) | (S)-2C$_9$-TR |
| 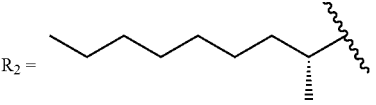 R$_2$ = ((R)-2C$_9$) | (R)-2C$_9$-TR |
| 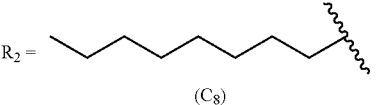 R$_2$ = (C$_8$) | C$_8$-TR |
| 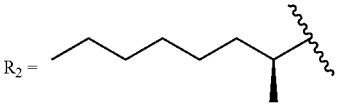 R$_2$ = ((S)-2C$_8$) | (S)-2C$_8$-TR |
| 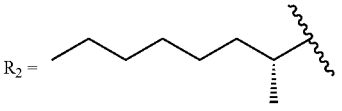 R$_2$ = ((R)-2C$_8$) | (R)-2C$_8$-TR |
| 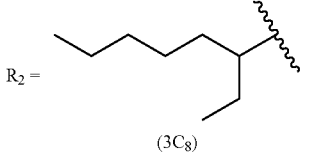 R$_2$ = (3C$_8$) | 3C$_8$-TR |
| 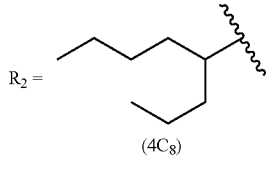 R$_2$ = (4C$_8$) | 4C$_8$-TR |
| 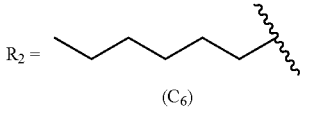 R$_2$ = (C$_6$) | C$_6$-TR |
| 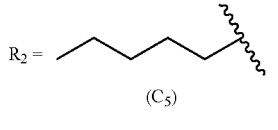 R$_2$ = (C$_5$) | C$_5$-TR |

TABLE 5-continued

| R₂ group | Compound abbreviation |
|---|---|
| R₂ = 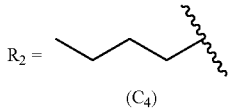 (C₄) | C₄-TR |
| R₂ = (C₃) | C₃-TR |
| R₂ = (C₂) | C₂-TR |

A general diagram for synthesis of the alkyl ester of treprostinil is shown in Scheme 1, below as well as FIG. 1. The alcohol can be modified based on the desired alkyl ester chain length (e.g., $C_5$-$C_{18}$ alkyl esters of even or odd chain length, straight chain or branched). Other reaction conditions used to synthesize treprostinil ester prodrugs are provided in Table 6, below.

Scheme 1: Esterification Mechanism for alkyl ester-TR Compounds

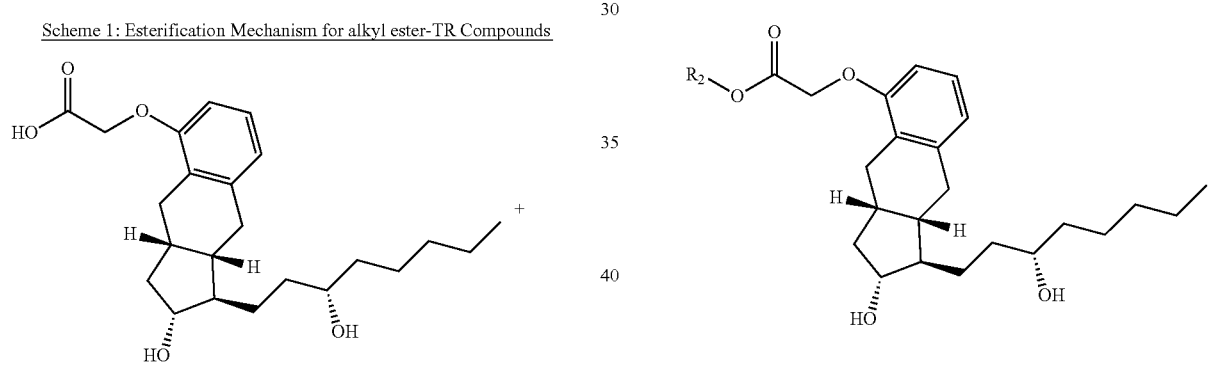

TABLE 6

| Entry | Ester | Solvent | Coupling Reagent | Additive | Time |
|---|---|---|---|---|---|
| 1 | C12TR | Dioxane (2 mL/100 μmol TRP) | DCC | DMAP | 84 h |
| 2 | C12TR | 10% DMF/DCM | DCC | DMAP | 84 h |
| 3 | C12TR | Dioxane (2 mL/100 μmol TRP) | Amberlyst-15 | — | 72 h |
| 4 | C12TR | Dioxane (1 mL/100 μmol TRP) | Amberlyst-15 | — | 18 h |
| 5 | C14TR | Dioxane (1 mL/100 μmol TRP) | Amberlyst-15 | — | 18 h |
| 6 | C14TR | Dioxane (1 mL/100 μmol TRP) | Amberlyst-15 | — | 18 h |
| 7 | C14TR | DMF | DCC | DMAP | 18 h |
| 8 | C14TR | DMF | PyBOP | TEA | 18 h |
| 9 | C14TR | DMF | HATU | TEA | 18 h |
| 10 | C14TR | Dioxane (2 mL/100 μmol TRP) | Amberlyst-15 | — | 168 h |
| 11 | 5C9TR | Dioxane (1 mL/100 μmol TRP) | Amberlyst-15 | — | 72 h |
| 12 | 5C9TR | Dioxane (1 mL/100 μmol TRP) | Amberlyst-15 | — | 72 h |
| 13 | 5C9TR | Dioxane (1 mL/100 μmol TRP) | Amberlyst-15 | — | 168 h |
| 14 | 5C9TR | 10% DMF/DCM | DCC | DMAP | 18 h |
| 15 | 5C9TR | 1:1 Dioxane:MeCN | HATU | — | 18 h |
| 16 | 5C9TR | 1:1 Dioxane:MeCN | PyBOP | — | 18 h |
| 17 | 5C9TR | DMF | HATU | — | 18 h |
| 18 | 5C9TR | DMF | PyBOP | — | 18 h |
| 19 | C16TR | Dioxane (1 mL/100 μmol TRP) | Amberlyst-15 | — | 18 h |

TABLE 6-continued

| Entry | Ester | Solvent | Coupling Reagent | Additive | Time |
|---|---|---|---|---|---|
| 20 | C16TR | DCM | DCC | DMAP | 18 h |
| 21 | C16TR | DCM | $PPh_3$, DEAD | — | 18 h |

DCC = N,N'-Dicyclohexylcarbodiimide;
DMAP = 4-dimethylaminopyridine
DMF = N,N'-dimethylformamide;
HATU = 1-[Bis(dimethylamino)methylene]-1H-1,2,3-triazolo[4,5-b]pyridinium 3-oxid Hexafluorophosphate;
PyBOP = benzotriazol-1-yl-oxytripyrrolidinophosphonium hexafluorophosphate Example 2—Acylation of Treprostinil Derivatives Treprostinil or treprostinil ester derivatives (e.g., derivatized with alkyl or alkenyl groups at the carboxylic acid moiety as prepared in Example 1) are acylated as follows.

The compound of Example 1 (0.05 mol) or treprostinil is dissolved in 10 mL of dichloromethane at 0° C. Dimethylaminopyridine is added (20 mol %), and then a solution of an acyl chloride R(CO)Cl (2.1 equivalents) at 0° C. (wherein R is $R_5$ or $R_6$ as described herein) is added to the compound of Example 1 or treprostinil. The solution is allowed to stir and warm to 23° C. over 1 hour. The reaction is monitored by thin layer chromatography, and when no further change is observed, the reaction is quenched with $NaHCO_3$ (sat), and the quenched mixture is extracted with dichloromethane (3×10 mL). The combined organic extracts are dried over anhydrous sodium sulfate, and the solvent is removed under vacuum to afford the crude product. Purification is effected by column chromatography on silica gel with 2% methanol in dichloromethane.

Figure 2:
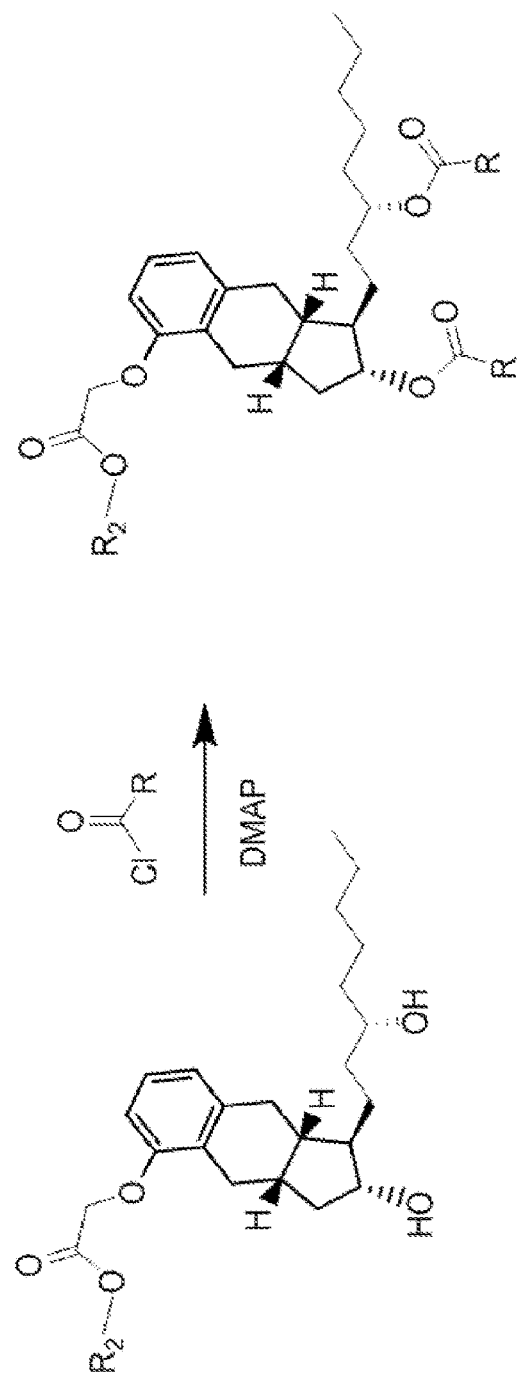
FIG. 2 is a general scheme for synthesis of acylated treprostinil derivative prodrugs.

A general scheme for synthesis of the acylated treprostinil prodrugs and treprostinil derivative prodrugs is shown below and in FIG. 2 ($R_2$ is described herein, for example as H or a linear or branched alkyl group):

Other acylation techniques known in the art, including selective acylation of each of the secondary alcohols, can be employed. In addition, $R_2$ can be selected such that the $R_2$ group can be selectively removed after acylation of the secondary hydroxyl functionalities. Such protecting group strategies are well known to those skilled in the art, and are described in, e.g., Peter G. M. Wutes and Theodora W. Greene, Greene's Protective Groups in Organic Synthesis, 4th Edition, Wiley (2006), which is incorporated herein by reference in its entirety for all purposes. An exemplary scheme of such a process is shown below:

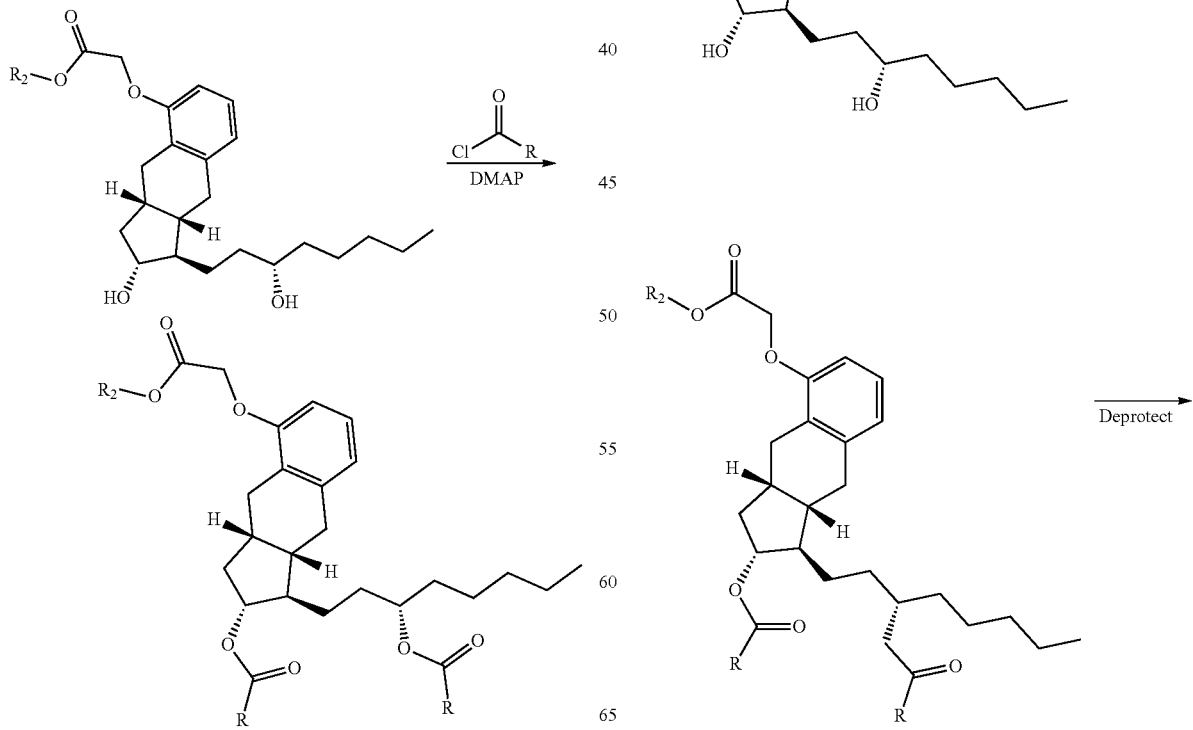

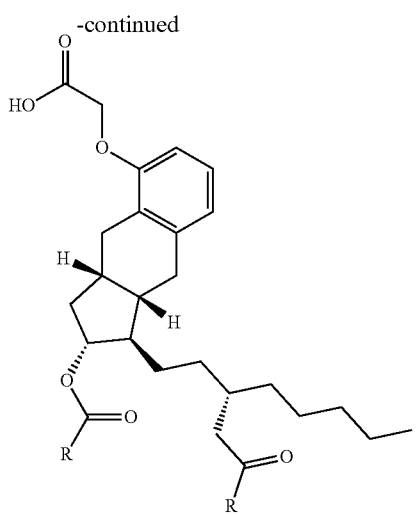

Synthesis of C₁₆TR-OAc:

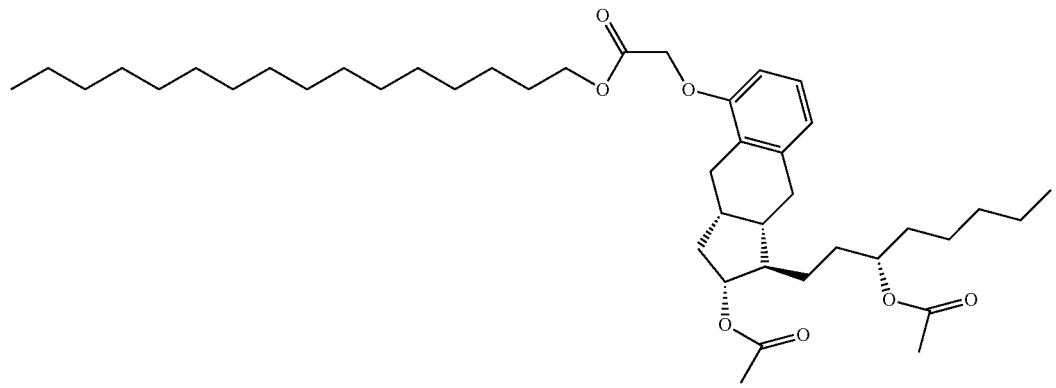 [SMILES: CCCCCCCCCCCCCCCCOC(=O)COc1cccc2c1C[C@H]1C[C@@H](OC(C)=O)[C@H](CC[C@H](CCCCC)OC(C)=O)[C@H]1C2]

To a solution of Hexadecyl Treprostinil (C16TR) (78.1 mg, 200 moles) dissolved in 1,4-Dioxane (2.0 mL) was added triethylamine (TEA) (98 μL, 700 moles, 3.5 equivalents), acetic anhydride (166 μL, 1,760 μmoles, 8.8 equivalents), and a catalytic amount of dimethylaminopyridine (DMAP). The reaction mixture was allowed to shake at 40° C. for 72 hours. Solvent was removed under reduced pressure to yield a thick colorless oil. The crude material was dissolved in hexanes and washed with a solution of saturated NaHCO₃ (3×5 mL). The organic layers were combined and solvent was removed using a gentle stream of warmed N₂ gas and gentle heat to yield a thick colorless oil. The crude material was dissolved in 20% ⁿPrOH/Hexanes, passed through a 0.45 μm syringe filter, and submitted to preparatory HPLC purification. Solvent was removed from the purified material using a gentle stream of warmed N₂ gas and gentle heat to yield a thick colorless oil. The pure material was suspended in ethyl lactate for storage and was submitted to analytical HPLC for concentration determination.

C₁₆-TR-OAc: 73% overall yield. The compound was also characterized by NMR spectroscopy:

¹H NMR (500 MHz, CDCl₃) δ 0.89 (t, J=7.0 Hz, 6H), 1.17-1.32 (m, 33H), 1.43-1.46 (m, 2H), 1.49-1.66 (m, 8H), 1.89-1.93 (m, 1H), 1.99 (s, 3H), 2.06 (s, 3H), 2.30-2.35 (m, 2h), 2.47 (d of d, J=14.5 Hz, J=6.0 Hz, 1H), 2.55 (d of d, J=15.0 Hz, J=6.0 Hz, 1H), 2.76 (d, of d, J=14.5 Hz, J=6.0 Hz, 1H), 2.90 (d of d, J=15.0 Hz, J=6.0 Hz, 1H), 4.19 (t, J=7.0 Hz, 2H), 4.62 (s, 2H), 4.70-4.74 (m, 1H), 4.87 (p, J=6.0 Hz, 1H), 6.63 (d, J=8.0 Hz, 1H), 6.82 (d, J=8.0 Hz, 1H), 7.08 (t, J=8.0 Hz, 1H) ppm; ¹³C NMR (125 MHz, CDCl₃) δ 14.2, 14.3, 21.5 (2), 22.7, 22.9, 25.1, 26.0 (2), 28.3, 28.8, 29.4, 29.6, 29.7, 29.8, 29.9, 31.9, 32.1, 33.6, 33.7, 34.3, 37.8, 40.7, 49.0, 65.6, 66.2, 74.6, 79.0, 109.8, 121.8, 126.4, 127.6, 140.7, 155.1, 169.6, 171.0, 171.1 ppm.

Example 3—Synthesis of Treprostinil Amide Derivatives

Treprostinil is available commercially, and can be synthesized, for example, by the methods disclosed in U.S. Pat. Nos. 6,765,117 and 8,497,393. Synthesis of prostaglandin derivatives is described in U.S. Pat. No. 4,668,814. The disclosures of U.S. Pat. Nos. 6,765,117; 8,497,393 and 4,668,814 are each incorporated by reference in their entireties for all purposes.

To a solution of (1R,2R,3aS,9aS)-[[2,3,3a,4,9,9α-hexahydro-2-hydroxy-1-[(3S)-3-hydroxyoctyl]-1H-benz[f]inden-5-yl]oxy]acetic acid (i.e., treprostinil) (78.1 mg, 200 μmoles) dissolved in 1,4-Dioxane (2.0 mL) was added triethylamine (TEA) (98 μL, 700 μmoles, 3.5 equivalents), alkylamine R₁—NH₂ (240 μmoles, 1.2 equivalents), and a solution of PyBOP (364 mg, 700 μmoles, 3.5 equivalents) dissolved in 2.0 mL MeCN (acetonitrile).

The reaction mixture was heated to 40° C. and allowed to shake at approximately 100 rpm overnight. Solvent was removed under reduced pressure to yield the crude product as a thick yellow oil. The product was extracted (1-1 extraction) from the oil by repeated washings with 20% ⁿPrOH/Hexanes (3×3 mL). Solvent was removed from the organic extract using a gentle stream of warmed N₂ gas and gentle heat to yield a thick, slightly yellow oil. The crude material was dissolved in 20% ⁿPrOH/Hexanes, passed through a 0.45 μm syringe filter, and submitted to preparatory HPLC purification. Solvent was removed from the purified material using a gentle stream of warmed N₂ gas and gentle heat to yield a thick, colorless oil. The pure material was suspended in ethyl lactate for storage and was submitted to analytical HPLC for concentration determination.

The following treprostinil amide derivatives of Formula (B) were made by the synthesis scheme provided above (Table 6). Percentage yield is also provided.

Formula (B)
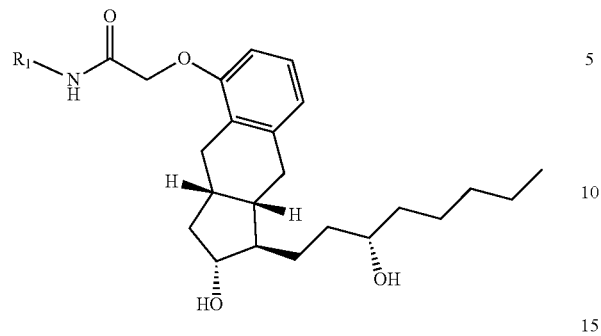
TABLE 7
Treprostinil amide derivatives
| $R_1$ group | Yield | Compound abbreviation |
|---|---|---|
| $R_1$ = ~~~~~~~~~~~~~~~~ ($C_{16}$) | 88% | $C_{16}$-TR-A |
| $R_1$ = ~~~~~~~~~~~~~~ ($C_{14}$) | 71% | $C_{14}$-TR-A |
| $R_1$ = ~~~~~~~~~~~~ ($C_{12}$) | 57% | $C_{12}$-TR-A |
| $R_1$ = ~~~~~~~~~~ ($C_{10}$) | 62% | $C_{10}$-TR-A |
| $R_1$ = ~~~~~~~~ ($C_8$) | 47% | $C_8$-TR-A |
| $R_1$ = (${}^tC_8$) | 72% | ${}^tC_8$-TR-A |
| $R_1$ = ~~~~~~ ($C_7$) | 50% | $C_6$-TR-A |
| $R_1$ = (${}^cC_7$) | 62% | ${}^cC_7$-TR-A |

TABLE 7-continued
Treprostinil amide derivatives
| $R_1$ group | Yield | Compound abbreviation |
|---|---|---|
| $R_1 =$ 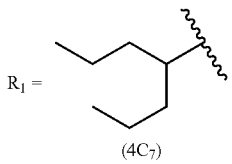 (4C$_7$) | 65% | 4C$_7$-TR-A |
| $R_1 =$ 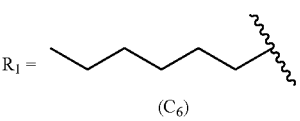 (C$_6$) | 58% | C$_6$-TR-A |
| $R_1 =$ 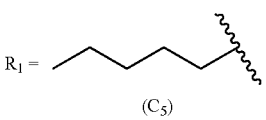 (C$_5$) | 77% | C$_5$-TR-A |
| $R_1 =$ 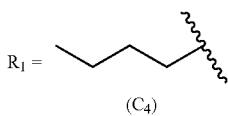 (C$_4$) | 28% | C$_4$-TR-A |
| $R_1 =$ 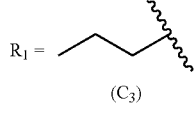 (C$_3$) | 12% | C$_3$-TR-A |
| $R_1 =$ 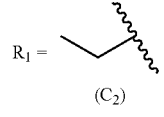 (C$_2$) | 12% | C$_2$-TR-A |
| $R_1 =$ 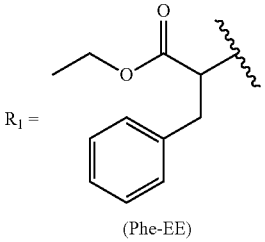 [SMILES: *C(Cc1ccccc1)C(=O)OCC] (Phe-EE) | 60% | Phe-EE-TR-A |
| $R_1 =$ 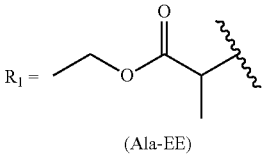 [SMILES: *C(C)C(=O)OCC] (Ala-EE) | Not determined | Ala-EE-TR-A |
| $R_1 =$ 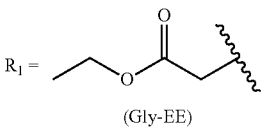 [SMILES: *CC(=O)OCC] (Gly-EE) | Not determined | Gly-EE-TR-A |

TABLE 7-continued

Treprostinil amide derivatives

| $R_1$ group | Yield | Compound abbreviation |
|---|---|---|
| $R_1 =$ (Leu-EE) | Not determined | Leu-EE-TR-A |

$C_6$-TR-A and $C_{12}$-TR-A were characterized by NMR spectroscopy.

NMR Characterization of C6-TR-A $^1$H NMR (500 MHz, CDCl$_3$) δ 0.90 (q, J=7.0 Hz, 6H), 1.17 (q, J=12.0 Hz, 1H), 1.30-1.70 (m, 18H), 1.81-1.83 (m, 1H), 1.80-1.93 (m, 1H), 2.20 (p, J=6.0 Hz, 1H), 2.22-2.23 (m, 1H), 2.47-2.54 (m, 2H), 2.75-2.82 (m, 2H), 3.16 (sextet, J=4.0 Hz, 1H), 3.35 (q, J=7.0 Hz, 2H), 3.63 (s, 1H), 3.70-3.80 (m, 1H), 4.48 (s, 2H), 6.55 (s, 1H), 6.70 (d, J=7.5 Hz, 1H), 6.85 (d, J=7.5 Hz, 1H), 7.11 (t, J=7.5 Hz, 1H) ppm; $^{13}$C NMR (125 MHz, CDCl$_3$) δ 14.2, 14.3, 22.8, 22.9, 25.6, 26.4, 26.7(2), 28.8, 29.7, 31.6, 32.1, 33.0, 33.8, 35.1, 37.7, 39.2, 41.4, 41.6, 46.5, 52.4, 68.4, 72.8, 110.4, 122.2, 126.8, 127.3, 141.2, 154.5, 168.7 ppm; HRMS (ESI, 2:2:1 MeCN, MeOH, H$_2$O): m/z=474.35717 ([M+H]$^+$).

NMR Characterization of C12-TR-A

HRMS (ESI, 2:2:1 MeCN, MeOH, H$_2$O): m/z=558.45099 ([M+H]$^+$).

While the described invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the described invention. All such modifications are intended to be within the scope of the claims appended hereto.

Patents, patent applications, patent application publications, journal articles and protocols referenced herein are incorporated by reference in their entireties, for all purposes.

The invention claimed is:

1. A method for making a treprostinil prodrug having the following formula:

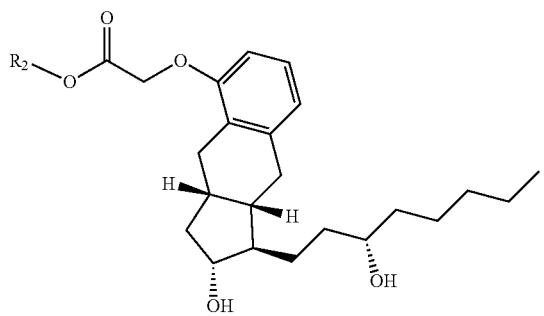

Formula (A)

comprising,
mixing, in the presence of an acid catalyst, treprostinil with an alcohol of the formula R$_2$—OH, wherein R$_2$ is a linear C$_{14}$-C$_{18}$ alkyl,
incubating the mixture for a sufficient period of time to form the compound of Formula (A).

2. The method of claim 1, wherein the treprostinil is dissolved in a solvent prior to mixing with the acid catalyst.

3. The method of claim 2, wherein the solvent comprises dioxane.

4. The method of claim 2, wherein the solvent comprises acetonitrile (MeCN), N,N'-dimethylformamide (DMF), dichloromethane (DCM), or a combination thereof.

5. The method of claim 2, wherein the solvent comprises 2 mL of dioxane per 100 μmol of treprostinil, 1 mL of dioxane per 100 μmol of treprostinil, DMF, DCM, MeCN, 1:1 dioxane:MeCN, DMF/DCM, 10% DMF/DCM, or 20% DMF/DCM.

6. The method of claim 1, wherein the acid catalyst is a solid.

7. The method of claim 6, wherein the solid is a solid resin.

8. The method of claim 1, wherein the acid catalyst comprises sulfuric acid, sulfonic acid, hydrofluoric acid, phosphoric acid, toluenesulfonic acid, polystyrene sulfonate, heteropoly acid, zeolites, metal oxides, graphene oxygen or a combination thereof.

9. The method of claim 1, wherein R$_2$ is linear hexadecyl.

10. The method of claim 1, wherein the acid catalyst is a sulfonic acid resin.

11. The method of claim 10, wherein R$_2$ is linear hexadecyl.

12. The method of claim 11, wherein the treprostinil is dissolved in a solvent prior to mixing with the acid catalyst.

13. The method of claim 12, wherein the solvent comprises dioxane.

14. The method of claim 1, wherein R$_2$ is linear tetradecyl.

15. The method of claim 1, wherein R$_2$ is linear pentadecyl.

16. The method of claim 1, wherein R$_2$ is linear heptadecyl.

17. The method of claim 1, wherein R$_2$ is linear octadecyl.

* * * * *